(12) United States Patent
Yoo et al.

(10) Patent No.: US 7,790,440 B2
(45) Date of Patent: Sep. 7, 2010

(54) SENSING SWITCH AND DETECTING METHOD USING THE SAME

(75) Inventors: Kyu-tae Yoo, Seoul (KR); Joon-ho Kim, Seongnam-si (KR); Jun-hong Min, Yongin-si (KR); Sung-ouk Jung, Suwon-si (KR); Ji-na Namgoong, Yongin-si (KR); Kui-hyun Kim, Daejeon-si (KR); Jeo-young Shim, Yongin-si (KR); Kak Namkoong, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 12/272,183

(22) Filed: Nov. 17, 2008

(65) Prior Publication Data

US 2009/0170211 A1 Jul. 2, 2009

Related U.S. Application Data

(62) Division of application No. 11/347,185, filed on Feb. 3, 2006, now Pat. No. 7,510,865.

(30) Foreign Application Priority Data

| Feb. 5, 2005 | (KR) | ........................ 10-2005-0010987 |
| Oct. 1, 2005 | (KR) | ........................ 10-2005-0092668 |

(51) Int. Cl.
*C12M 3/00* (2006.01)
(52) U.S. Cl. .................................... 435/287.2; 436/526
(58) Field of Classification Search .................. None
See application file for complete search history.

(56) References Cited

U.S. PATENT DOCUMENTS

| 5,807,758 | A | 9/1998 | Lee et al. |
| 6,090,933 | A | 7/2000 | Kayyem et al. |
| 6,096,273 | A | 8/2000 | Kayyem et al. |
| 2004/0058335 | A1 | 3/2004 | Su et al. |

FOREIGN PATENT DOCUMENTS

| EP | 0106873 | B1 | 1/1986 |
| JP | 1992369418 | A | 12/1992 |
| JP | 1999038023 | A | 2/1999 |
| JP | 2004506872 | A | 3/2004 |
| WO | 9850773 | A2 | 11/1998 |
| WO | 9852043 | A1 | 11/1998 |
| WO | 2004029625 | A2 | 4/2004 |

OTHER PUBLICATIONS

Baselt et al., ["A High-Sensitivity Micromachined Biosensor", Proceedings of the IEEE, vol. 85, No. 4, Apr. 1997, p. 672-680].*
Raiteri et al., ["Micromechanical cantilever-based biosensors", Sensors and Actuators B 79 (2001), p. 115-126].*
Raiteri, et al., Micromechanical Cantilever-based Biosensors, Sensors and Actuators, B 79 (2001), 115-126.
European Search Report dated Sep. 1, 2006 for Application No. 06001893.4-2404 ( All references cited in Search Report are cited above.).
"A High-Sensitivity Micromachined Biosensor"; BASELT, et al.; Proceedings of the IEEE; vol. 85, No. 4; pp. 672-680; Apr. 1997.
"The effect of surface probe density on DNA hybridization"; Peterson, et al.; Nucleic Acids Research; vol. 29, No. 24; pp. 5163-5168; 2001.
"Probing Biomolecule Recognition with Electron Transfer: Electrochemical Sensors for DNA Hybridization"; Napier, et al.; Bioconjugate Chem.; vol. 8; pp. 906-913; 1997.
"Novel DNA sensor for electrochemical gene detection"; Hashimoto, et al.; Analytica Chimica Acta; vol. 286; pp. 219-224; 1994.
"Electrochemical Quantitation of DNA Immobilized on Gold"; Steel, et al.; Anal. Chem.; vol. 70; pp. 4670-4677; 1998.
Photoinduced Electron Transfer in Ethidium-Modified DNA Duplexes: Dependence on Distance and Base Stacking; Kelley, et al.; J. Am. Chem. Soc.; vol. 119; pp. 9861-9870; 1997.

* cited by examiner

*Primary Examiner*—Ann Y Lam
(74) *Attorney, Agent, or Firm*—Cantor Colburn LLP

(57) ABSTRACT

Provided are a sensing switch and a sensing method using the same. The sensing switch includes: a substrate; a supporter on the substrate; a sensing plate that is connected to a side of the supporter and is in parallel with the substrate by a predetermined distance; a receptor binding region on an upper surface of an end portion of the sensing plate; an electric or magnetic field generation device that induces deflection of the sensing plate when a receptor bound to the receptor binding region is selectively bound to an electrically or magnetically active ligand; and a pair of switching electrodes that are separated by a predetermined distance and is connected when the sensing plate contacts the substrate due to the deflection of the sensing plate. A target material need not be labelled, a signal processing of a fluorescent or electrical detection signal using an analysis apparatus is not required, and a signal can be directly decoded by confirming whether a current flows through the switch.

6 Claims, 23 Drawing Sheets

NO CURRENT FLOW

SENSING SWITCH AND DETECTING METHOD USING THE SAME

CROSS-REFERENCE TO RELATED PATENT APPLICATIONS

This application is a divisional application of U.S. application Ser. No. a 11/347,185, filed Feb. 3, 2006, which claims the benefit of Korean Patent Application Nos. 10-2005-0010987 filed on Feb. 5, 2005, and 10-2005-0092668 filed on Oct. 1, 2005, in the Korean Intellectual Property Office, the disclosures of which are incorporated herein in their entirety by reference.

BACKGROUND OF THE INVENTION

1. Field of the Invention

The present invention relates to an apparatus for sensing a biomolecule or a chemical material, and more particularly, to a sensing switch that physically moves due to an electrostatic force between an electrode having the same polarity as a ligand and another electrode having the opposite polarity to the ligand or due to a magnetic force between a magnetic bead bound to a ligand and a magnetic field generation device, thus acting as a switch, and a sensing method using the same.

2. Description of the Related Art

Effective sensing of biomolecules and chemical materials is required in a wide range of applications, such as biochips. A biochip is formed by immobilizing a receptor (biomolecules), such as DNA or a protein, with high density on a support, and can be used to analyze gene expression characteristics, gene defects, protein distribution, reaction characteristics, and the like. Biochips are categorized into microarray chips and lab-on-a-chips according to where a receptor is affixed. A microarray chip is formed by affixing a receptor to a solid support, and a lab-on-a-chip is formed by affixing a receptor to a microchannel. In order to find a target material in a sample able to bind to a receptor immobilized on a support, the biochip requires a system that can detect whether a receptor immobilized on a support.

In general, a DNA chip for gene analysis is used to analyze a gene by labeling a sample DNA with a fluorescent pigment, reacting the labeled sample DNA with a receptor on the chip, and detecting the fluorescent material remaining on the surface of the chip using a confocal microscope and a CCD camera (See U.S. Pat. No. 6,141,086). However, it is difficult to miniaturize the equipment required for such an optical sensing method and the result cannot be digitally output. Therefore, much research has been conducted to develop a new method in which the analysis result can be output via an electrical signal.

A method of and apparatuses for electrochemically detecting DNA hybridization using a metal compound, which can be easily oxidized and reduced, has been researched in many labs including a Clinical Micro Sensor (See U.S. Pat. Nos. 6,096,273 and 6,090,933). In this case, when DNA is hybridized, another compound containing a metal that can be easily oxidized and reduced is combined with the hybridized DNA to form a complex, which is electrochemically detected [*Anal. Chem.*, Vol. 70, pp. 4670-4677, 1998; *J. Am. Chem. Soc.*, Vol. 119, pp. 9861-9870, 1997; *Analytica Chimica Acta*, Vol. 286, pp. 219-224, 1994; and *Bioconjugate Chem.*, Vol. 8, pp. 906-913, 1997.] However, the electrochemical methods also require a labeling process.

In addition, a conventional fluorescent or electrochemical sensing method requires a sensor, a measuring apparatus for measuring the output of the sensor, and an analysis device for processing a signal obtained from the measuring apparatus. Therefore, the entire system is bulky, many expensive apparatuses are required, and skilled engineers are required to perform each operation. Even when all these requirements are complied with, it takes a long time to obtain a final result and a noise is guaranteed in connections between apparatuses.

In order to overcome these problems, the inventors of the present invention confirmed that a sensor can physically moves due to an electrostatic force between an electrode having the same polarity as a ligand and another electrode having an opposite polarity to the ligand or due to a magnetic force between a magnetic bead bound to a ligand and a magnetic field generation device, thus acting as a switch, so that a miniaturized sensing switch that needs not require signal processing can be manufactured.

SUMMARY OF THE INVENTION

The present invention provides a sensing switch that can perform mechanical sensing and electrical switching at the same time and does not require signal processing after the sensing.

The present invention also provides a sensing circuit including a plurality of sensing switches that are connected in the form of a logic circuit.

The present invention also provides a method of sensing whether a ligand is bound using the sensing switch.

According to an aspect of the present invention, there is provided a sensing switch including: a substrate; a supporter on the substrate; a sensing plate that is connected to a side of the supporter and is in parallel with the substrate by a predetermined distance; a receptor binding region on an upper surface of an end portion of the sensing plate; an electric or magnetic field generation device that induces deflection of the sensing plate when a receptor bound to the receptor binding region is selectively bound to an electrically or magnetically active ligand; and a pair of switching electrodes that are separated by a predetermined distance and is connected when the sensing plate contacts the substrate due to the deflection of the sensing plate.

According to another aspect of the present invention, there is provided a sensing switch including: a substrate; a supporter on the substrate; a sensing plate that is connected to a side of the supporter and is in parallel with the substrate by a predetermined distance; a receptor binding region on an upper surface of an end portion of the sensing plate; a push-out electrode that has the same polarity as a ligand above the sensing plate; a pull-in electrode that has the opposite polarity to the ligand below the sensing plate; and a pair of switching electrodes that are separated by a predetermined distance and is connected when the sensing plate contacts the substrate due to respective repulsive and attractive forces of the push-out electrode and the pull-in electrode.

According to still another aspect of the present invention, there is provided a sensing switch including: a substrate; a supporter on the substrate; a sensing plate that is connected to a side of the supporter and is in parallel with the substrate by a predetermined distance; a receptor binding region on an upper surface of an end portion of the sensing plate; a magnetic bead that is selectively bound to a receptor bound to the receptor binding region through a ligand; a magnetic field generation device below the sensing plate; and a pair of switching electrodes that are separated by a predetermined distance and is connected when the sensing plate contacts the substrate due to a magnetic field generated by the magnetic field generation device.

The sensing plate may be a cantilever or seesaw-type lever (like a seesaw), and preferably, the seesaw-type lever. When the sensing plate is the seesaw-type lever, the sensing plate may extend in opposite directions from the center of a connecting beam which connects two supports formed on the substrate, and is in parallel with the substrate by a predetermined distance, and two receptor binding regions can be formed on upper surfaces of arms of the sensing switch. The arms of the sensing plate move up and down in the same manner as a seesaw, thus connecting and separating the switching electrodes that are separated from each other by a predetermined distance.

The supporter may support the connecting beam or the sensing plate that is in parallel with the substrate by a predetermined distance and may act as a pivot for rotation of the connecting beam.

The sensing plate may be composed of a material such that the sensing plate can be easily bent by the respective repulsive and attractive forces of the push-out electrode and the pull-in electrode. Therefore, the entire sensing plate or at least a portion of the sensing plate contacting the switching electrode may be composed of an electrical conducting material so that the switching electrodes on the substrate can be connected to each other when the sensing plate is bent downward.

The connecting beam may be narrower and thinner than the sensing plate, and thus can be easily bent by the respective repulsive and attractive forces of the push-out electrode and the pull-in electrode. The connecting beam may be integrated with or separated from the sensing plate.

The ligand may be a biomolecule or chemical material, which is electrically charged. For example, the ligand may be a nucleotide, a protein, a peptide, an antibody, an antigen, or a liquid or vapour chemical material, which may be selectively bound to the receptor.

The ligand can be directly bound to the receptor binding region. Alternatively, a receptor that can be bound to a ligand can be bound to the receptor binding region. In the latter case, the receptor can be any receptor that can bond to the ligand, and may be DNA, RNA, peptide nucleic acid (PNA), locked nucleic acid (LNA), a protein, a peptide, or a chemical material. In the present specification, the term 'the binding' indicates a specific binding, such as hybridisation of a nucleic acid and Ag-Ab interaction.

The receptor binding region may be made of any material to which a biomolecule or a chemical material can bond. For example, the receptor binding region may be made of a material selected from glass, metal, plastic, and silicon. In addition, the surface of the receptor binding region can be modified to have —COOH, —SH, —OH, a silane group, an amine group, or an epoxy group using a conventional biochip surface modification method so as to allow the receptor or the ligand to be bound.

A ligand that is to be selectively bound to a receptor, or a secondary receptor that is to be selectively bound to the ligand may be adhered to the magnetic bead.

The receptor may be immobilized on one of two receptor binding regions. Preferably, different ligands are respectively immobilized on the two receptor binding regions. In this case, one of two ligands may act as a reference receptor and thus differential detection can be performed and a background signal can be effectively removed.

According to another aspect of the present invention, there is provided a sensing circuit that forms 'AND' and/or 'OR' logic circuits by arranging a plurality of sensing switches according to the present invention in series and/or parallel.

In the 'AND' logic circuit, at least two sensing switches are connected in series. In this case, a current flows only when all of the switches are closed. In the 'OR' logic circuit, at least two sensing switches are connected in parallel. In this case, a current flows only when at least one of the switches is closed. In the present invention, various logic circuits can be formed by combining the plurality of 'AND' and/or 'OR' logic circuits.

The sensing circuit may performs sensing and analyzing at the same time in response to output signals from the 'and/or' logic circuits. The sensing circuit may have at least one input line and at least one output line. The sensing and analyzing of a plurality of receptors can be performed at the same time by applying a current to the input line and measuring the current from each output line. In addition, the signal processing is not required after the signal sensing. That is, the binding of the different receptors in sensing switches forming a circuit can be effectively analyzed by only confirming whether a current is output from the output line, for example, whether a lamp is on or off, without processing the sensed signal.

According to yet another aspect of the present invention, there is provided a method of sensing ligand binding, the method including: providing a ligand to a receptor binding region of the sensing switch; binding the ligand, and a receptor immobilized on the receptor binding region; applying a voltage that has the same polarity as the ligand to a push-out electrode and a voltage that has an opposite polarity to the ligand to a pull-in electrode; raising and lowering the sensing plate in response to the respective repulsive and attractive forces between the push-out electrode and the pull-in electrode and the ligand so that the pair of switching electrodes are connected or separated; and sensing whether a current flows between the switching electrodes.

According to another aspect of the present invention, there is provided a method of sensing ligand binding, the method including: adhering a magnetic bead to a ligand that is to be selectively bound to a receptor or a secondary receptor that is to be selectively bound to the ligand; providing to the receptor binding region of the sensing switch the ligand or secondary receptor adhered to the magnetic bead; adhering the magnetic bead to the receptor binding region by selectively binding the ligand and the receptor; removing the ligand or second receptor adhered to a magnetic bead that is not bound to the receptor binding region; generating an electric field by using an electric field generation device below the sensing plate; raising and lowering the sensing plate in response to the generated magnetic field so that the pair of switching electrodes are connected or separated; and sensing whether a current flows between the switching electrodes.

A receptor may be immobilized on only one of two receptor binding regions of the sensing switch. Preferably, different ligands may be respectively immobilized on two receptor binding regions such that differential binding of the different ligands can be sensed. In this case, the two receptor binding regions move like a seesaw such that an end of a sensing plate to which more receptors are bound descends. At this time, one of two kinds of ligands acts as a reference receptor, and thus a background signal can be effectively removed.

In a conventional electrical sensing method, resistance, impedance, the amount of a current, and the like are measured using a measuring apparatus and then signal processing is performed. On the other hand, according to the present invention, the binding of a receptor can be easily identified by confirming whether a current flows through a sensing switch or not, for example, by confirming whether a lamp is on or off.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings.

Figure 1:
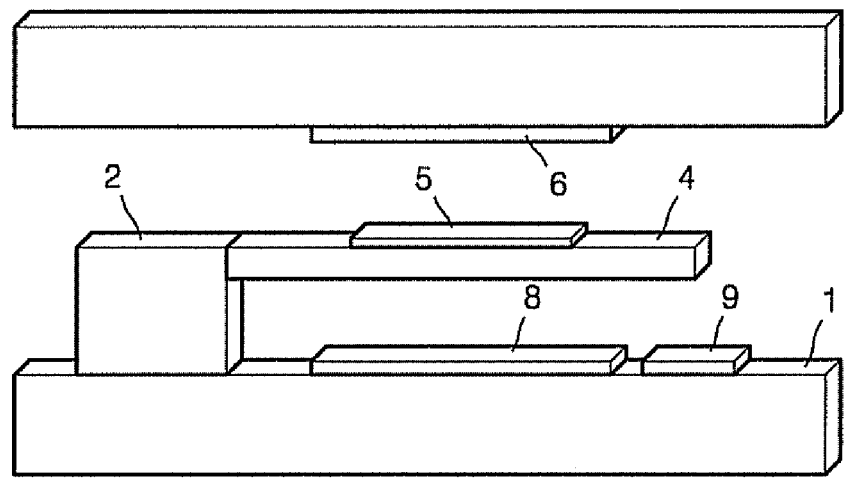
FIG. 1 is a front view of a sensing switch (cantilever) according to an embodiment of the present invention.

FIG. 1 is a front view of a sensing switch (cantilever) according to an embodiment of the present invention. Referring to FIG. 1, the sensing switch includes a substrate 1, a supporter 2 formed on the substrate 1, a sensing plate 4 that is connected to a side of the supporter 2 and is in parallel with the substrate 1 by a predetermined interval, a receptor binding region 5 formed on an upper surface of the sensing plate 4, a push-out electrode 6 that has the same polarity as a ligand and disposed above the sensing plate 4, a pull-in electrode that has the opposite polarity to the ligand and disposed below the sensing plate 4, and a pair of switching electrodes 9 that are separated by a predetermined interval and can be connected to each other when the sensing plate 4 contacts the substrate 1 due to a repulsive force and an attractive force of the push-out electrode 6 and the pull-in electrode 8.

In FIG. 1, to the receptor binding region 5, a ligand able to bond with a receptor can be directly immobilized. When the ligand is directly or indirectly immobilized on the receptor binding region 5, a repulsive force occurs between the ligand and the push-out electrode 6 because the target molecule and the push-out electrode 6 have the same polarity and an attractive force occurs between the ligand and the pull-in electrode 8 because the ligand and the pull-in electrode 8 have opposite polarities, and thus the sensing plate 4 is bent downward. At this time, an end of the sensing plate 4 contacts the switching electrodes 9 and thus a current flows.

Although the switching electrodes 9 are illustrated as a single unit in FIG. 1, they are separated by a predetermined distance. Thus, before the sensing plate 4 contacts the switching electrodes 9, the current does not flow.

Figure 2:
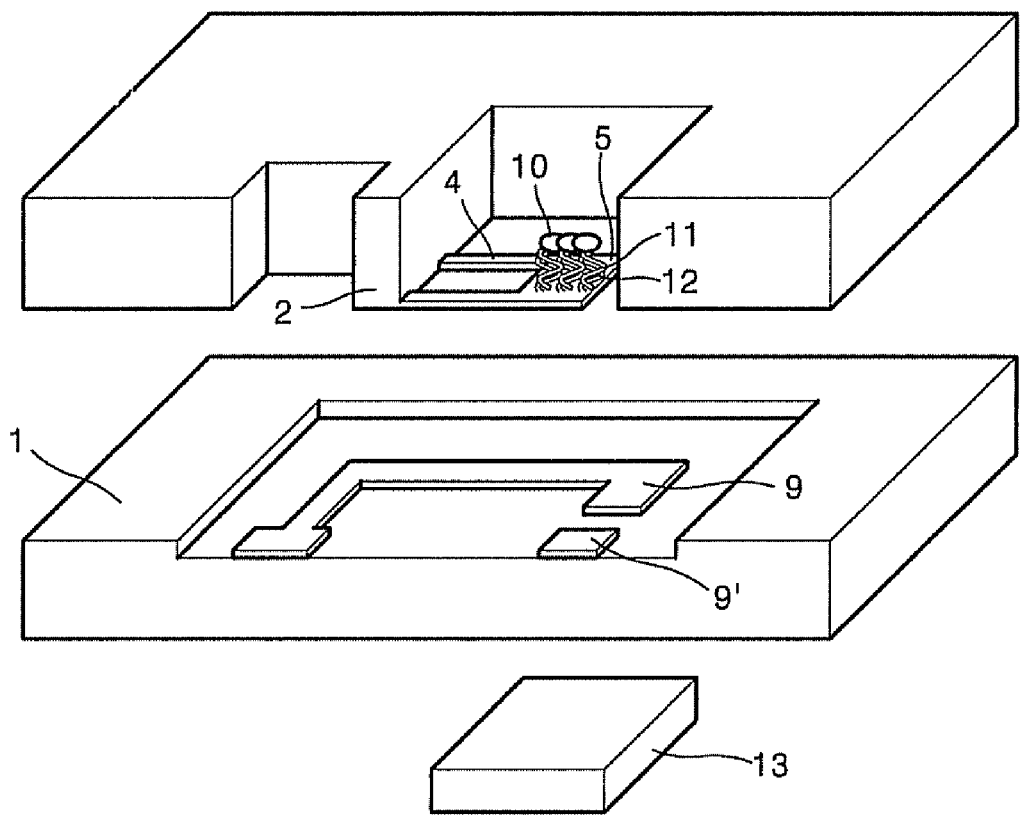
FIG. 2 is an exploded perspective view of a sensing switch (cantilever) according to another embodiment of the present invention.

FIG. 2 is an exploded perspective view of a sensing switch (cantilever) according to another embodiment of the present invention. Referring to FIG. 2, the sensing switch includes a substrate 1; a supporter 2 on the substrate 1; a sensing plate 4 that is connected to a side of the supporter 2 and is in parallel with the substrate 1 by a predetermined distance; a receptor binding region 5 on an upper surface of an end portion of the sensing plate 4; a magnetic bead 10 that is selectively bound to a receptor 12 bound to the receptor binding region 5 through a ligand 11; a magnetic field generation device 13 below the sensing plate 4; and a pair of switching electrodes 9 and 9' that are separated by a predetermined distance and is connected when the sensing plate 4 contacts the substrate 1 due to a magnetic field generated by the magnetic field generation device 13.

In FIG. 2, the receptor 12 is immobilized on the receptor binding region 5, the magnetic bead 10 is bound to the ligand 11, and the magnetic bead 10 is bound to the receptor binding region 5 on the upper surface of an end of the sensing plate 4 through selective binding between the ligand 11 and the receptor 12. The magnetic bead 10 bound to the receptor binding region 5 moves toward the substrate 1 due to a magnetic field generated by the magnetic field generation device 13 and thereby, the sensing plate 4 bends.

The magnetic bead may be in a form of suspension, and can be obtained from, for example, Dynal AS Inc. The magnetic bead may include a ferromagnetic bead, a paramagnetic bead, and a super-paramagnetic bead. The magnetic bead can be prepared using a method disclosed in EP No. 0106873.

Figure 3A:
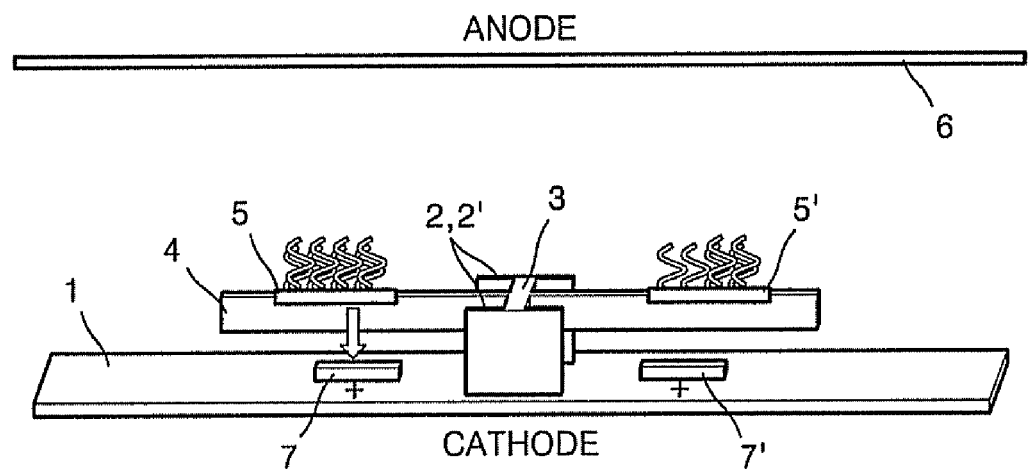
FIG. 3A is a front view of a sensing switch (seesaw-type lever) according to another embodiment of the present invention.
Figure 3B:
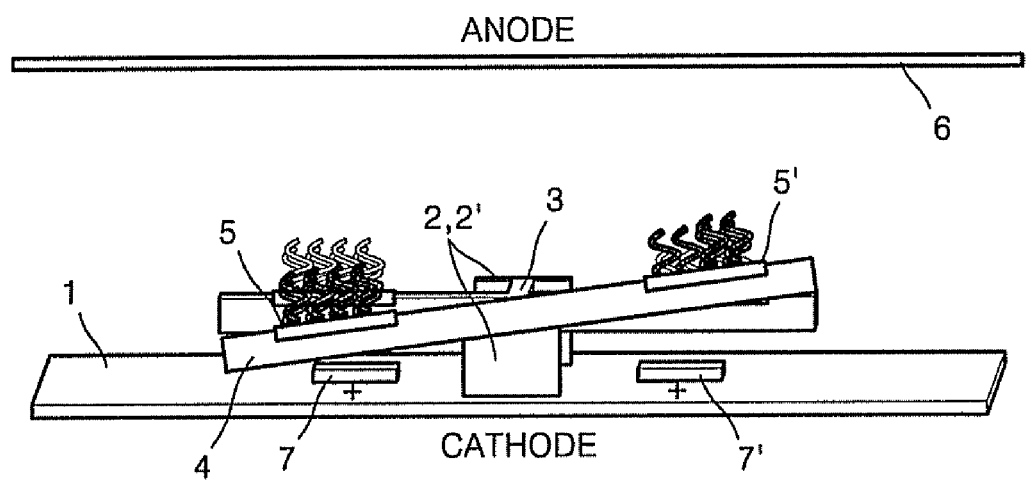
FIG. 3B illustrates an operation of the switch when sensed.

FIG. 3A is a front view of a sensing switch (seesaw-type lever) according to another embodiment of the present invention, and FIG. 3B illustrates an operation of the switch shown in FIG. 3A when sensed. Referring to FIGS. 3A and 3B, the sensing switch includes a substrate 1, two supporters 2 and 2', a connecting beam 3 connecting the supporters 2 and 2', a sensing plate 4 that crosses the center of the connecting beam 3 and is in parallel with the substrate 1 by a predetermined distance, receptor binding regions 5 and 5' formed on upper surfaces of two arms of the sensing plate 4, a push-out electrode 6 that has the same polarity as the ligand and disposed above the sensing plate 4, pull-in electrodes 7 and 7' that have opposite polarities to the ligand and are disposed below the sensing plate 4, and a pair of switching electrodes (not shown) that are separated by a predetermined interval and can be connected to each other when the sensing plate 4 contacts the substrate 1 due to a repulsive force and an attractive force of the push-out electrode 6 and the pull-in electrodes 7 and 7'.

Referring to FIG. 3A, different receptors, such as oligonucleotide, are respectively immobilized on the receptor binding regions 5 and 5', and more target DNA molecules are immobilized on the receptor binding region 5 than the receptor binding region 5'. As a result, the receptor binding region 5 is more negatively charged than the receptor binding region 5'. The push-out electrode 6 disposed above the sensing plate 4 is an anode with the same polarity as that of DNA, and the pull-in electrodes 7 and 7' disposed below the sensing plate 4 are cathodes with the opposite polarity to that of DNA. The pull-in electrodes 7 and 7' can be separate or integrated. In FIG. 3B, since the receptor binding region 5 exhibits a greater negative charge than the receptor binding region 5', the sensing plate 4 is inclined due to effective electrostatic forces between the negative push-out electrode 6 and the positive pull-in electrode 7, that is, a repulsive force and attractive force, thus having a seesaw motion.

Figure 3C:
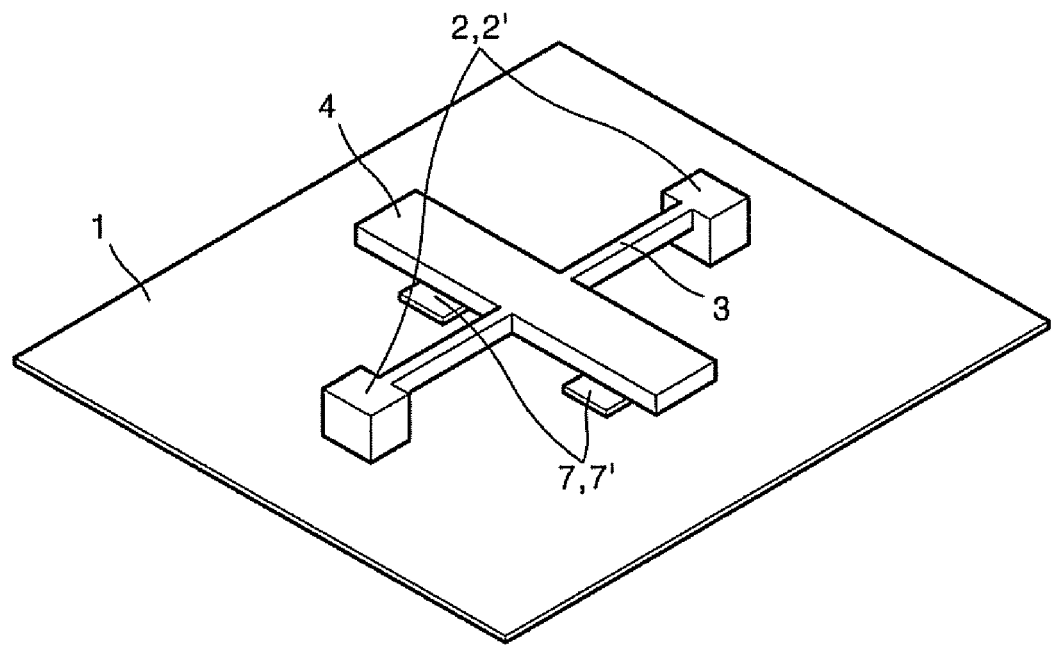
FIG. 3C is a perspective view of a sensing switch according to another embodiment of the present invention.

FIG. 3C is a perspective view of a sensing switch according to another embodiment of the present invention. Referring to FIG. 2C, detailed descriptions of the receptor binding regions 5 and 5' formed on the upper surfaces of the two arms of the sensing plate 4, the push-out electrode 6 disposed above the sensing plate 4, the pull-in electrodes 7 and 7' disposed below the sensing plate 4, and the switching electrodes disposed on the substrate 1 are not illustrated.

Figure 4A:
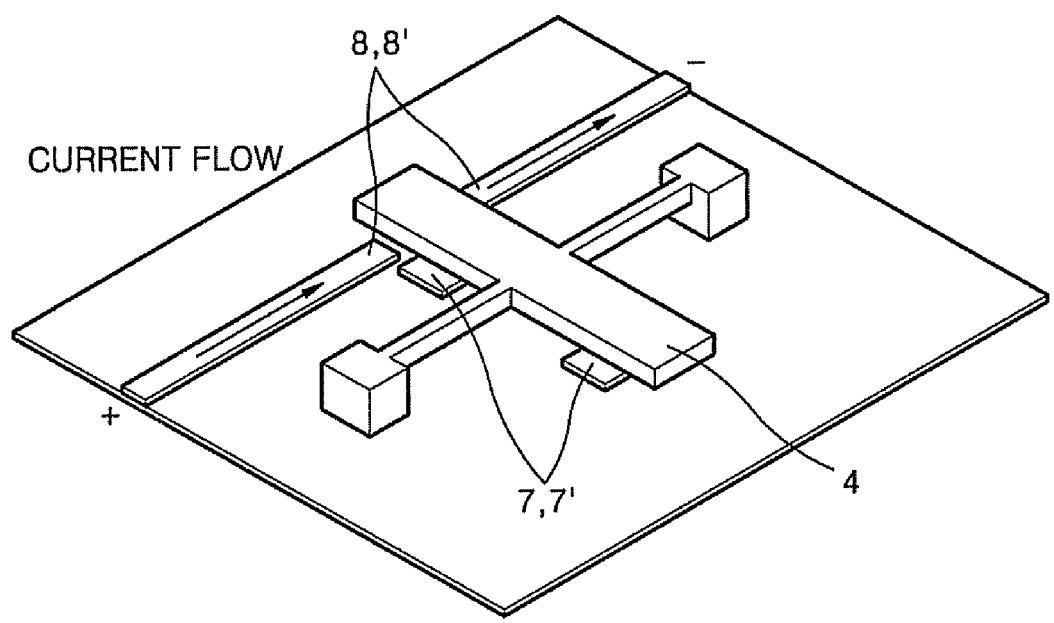
FIG. 4A is a schematic view when the sensing switch shown in FIG. 3A is closed.
Figure 4B:
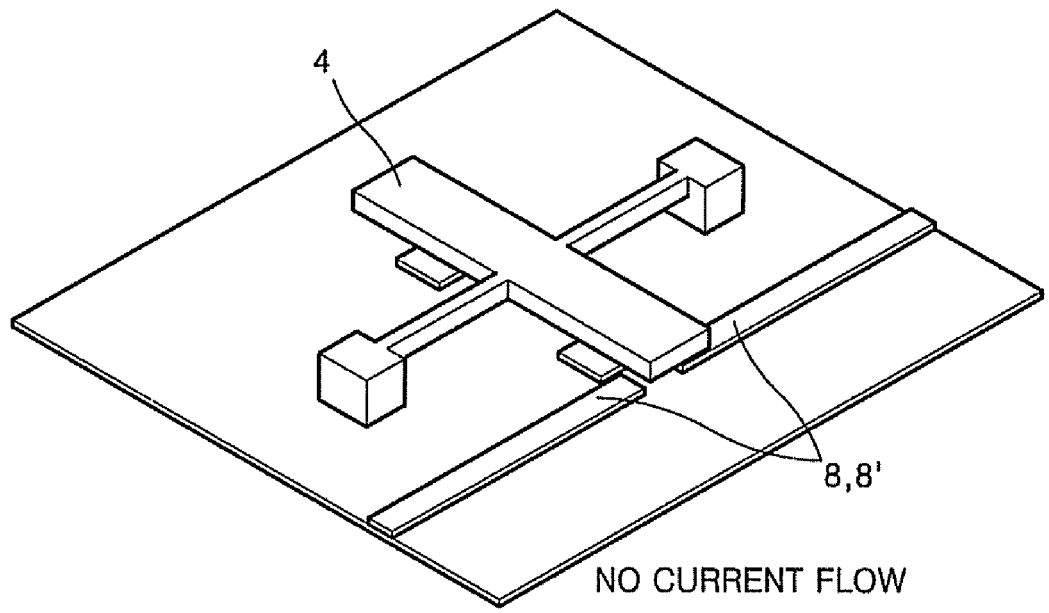
FIG. 4B is a schematic view when the sensing switch shown in FIG. 3A is open.

FIG. 4A is a schematic view when the sensing switch shown in FIG. 3A closed, and FIG. 4B is a schematic view when the sensing switch shown in FIG. 3A is open. Referring to FIGS. 4A and 4B, when the switch is closed, the current flows between switching electrodes on the substrate; and when the switch is open, the current does not flow between the switching electrodes on the substrate. Accordingly, the sensing switch can act as a sensor and a switch at the same time. In other words, when the ligand is immobilized on the receptor binding regions 5 and 5', the electric charge on the receptor binding regions 5 and 5' is changed and the switch is closed. As described above, since the sensing switch according to an embodiment of the present invention can be closed or open, a logic circuit, such as a common electric circuit, can be manufactured.

Since the sensing switch can perform mechanical sensing and electrical switching at the same time, a signal processing subsequent to the sensing is not required. In addition, the sensing switch requires minimal circuitry and power, and thus it can be more miniaturized than a conventional apparatus performing sensing and signal processing switch. Further, the sensing switch produces minimal circuit noise, such as flicker and white noise, and the noise can be minimized by eliminating a connection noise between a sensor and a post processor since a post processor is not required.

Figure 5A:
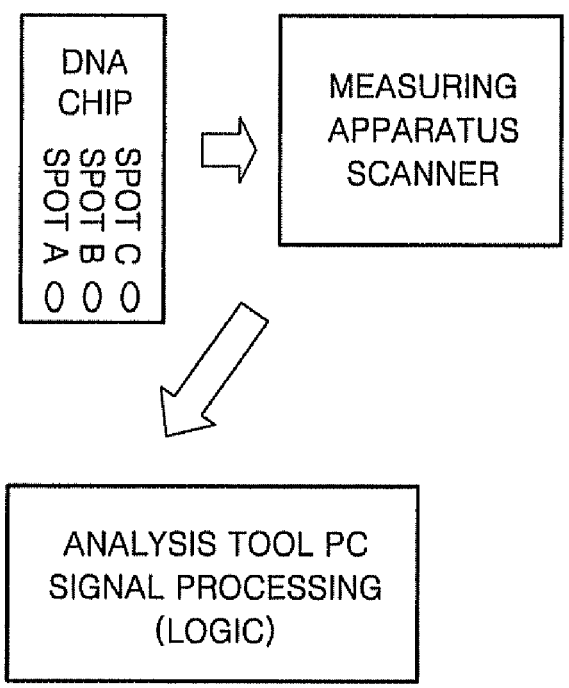
FIG. 5A is a schematic view of a conventional DNA chip detection system.
Figure 5B:
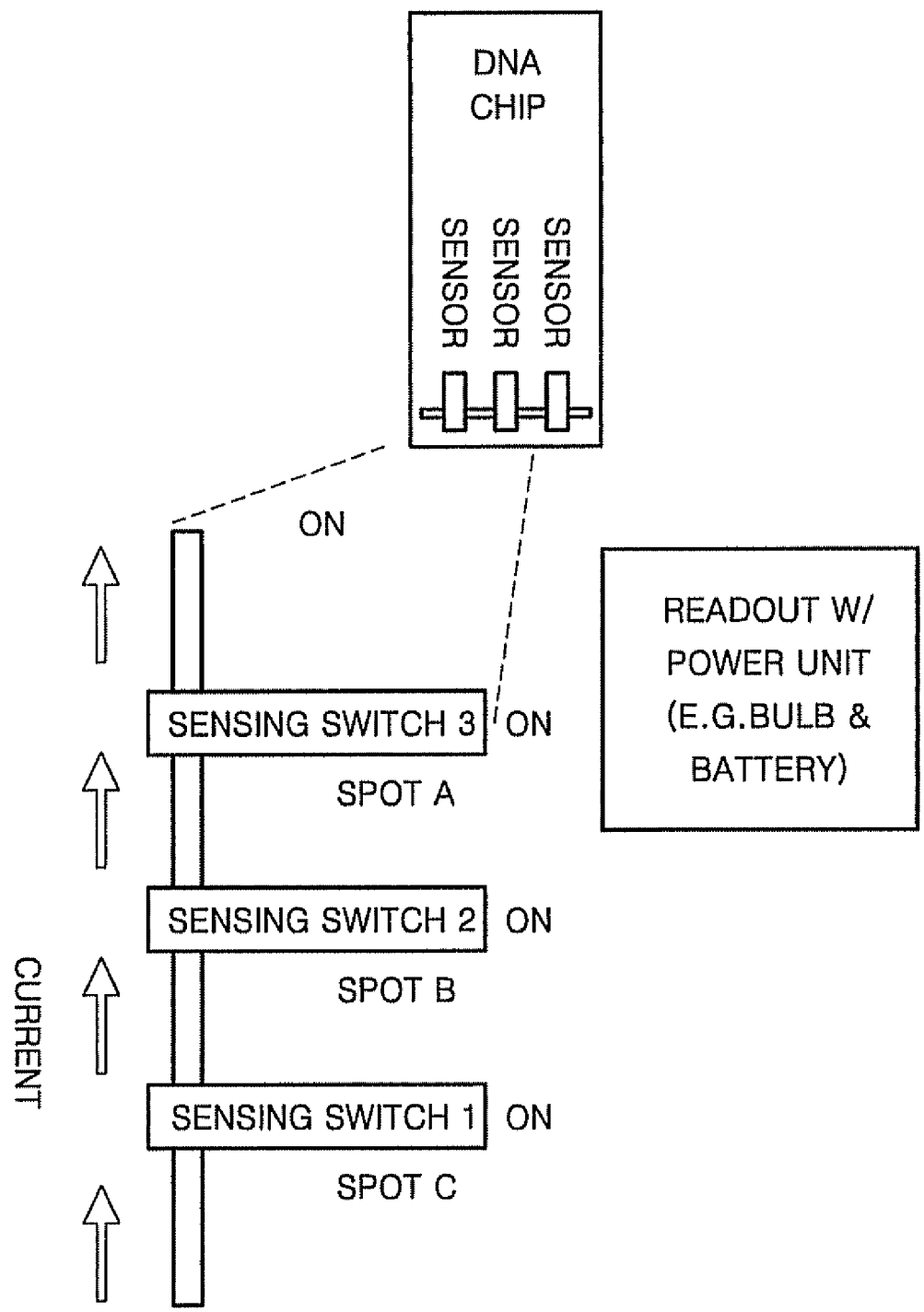
FIG. 5B is a schematic view of a DNA chip detection system according to an embodiment of the present invention.

FIG. 5A is a schematic view of a conventional DNA chip detection system, and FIG. 5B is a schematic view of a DNA chip detection system according to an embodiment of the present invention. Referring to FIG. 5A, when spots A, B, and C on a DNA chip are scanned and a signal is processed using an analysis apparatus, the spots A, B, and C exhibit an intensity greater than a predetermined level. As a result, whether a target patient is a MODY patient can be identified. However, referring to FIG. 5B, according to an embodiment of the present invention, three sensing switches on a single DNA chip perform sensing and analysing and whether a final output line is closed is confirmed using a simple apparatus, such as a lamp. As a result, whether a target patient is a MODY patient can be identified.

Figure 6A:
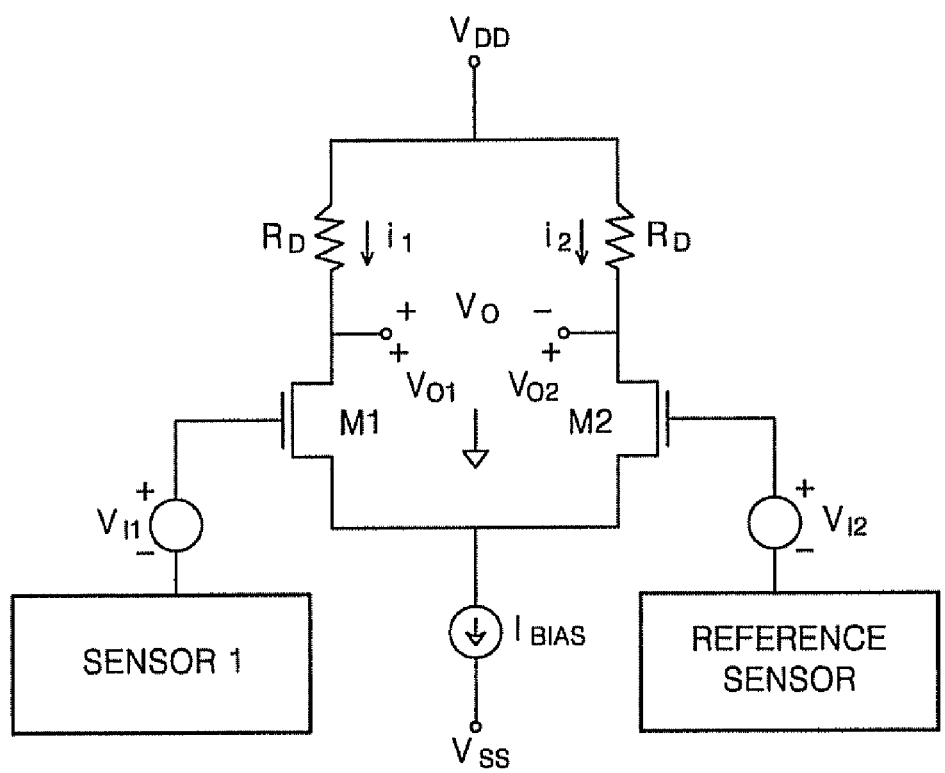
FIG. 6A is a schematic diagram of a conventional differential sensing system.
Figure 6B:
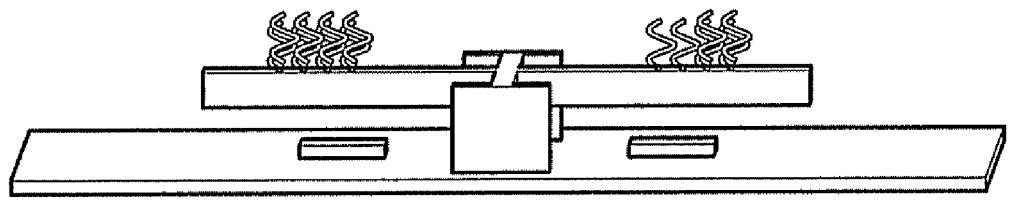
FIG. 6B is a perspective view of a differential sensing system according to an embodiment of the present invention.

FIG. 6A is a schematic diagram of a conventional differential sensing system, and FIG. 6B is a perspective view of a differential sensing system according to an embodiment of the present invention. The differential sensing system decreases a low common noise factor/background noise, and thus decreases a high S/N ratio. A conventional differential sensing system includes an analysis sensor and a reference spot/sensor (identical) as shown in FIG. 6A, and the results output by the sensors are analyzed using an analytical tool/electrical circuit. Therefore, the conventional differential sensing system requires at least two identical spot/sensor, and differential amplification/post analysis of an acquired signal. On the other hand, referring to FIG. 6B, the differential sensing system according to an embodiment of the present invention can be miniaturized, consume minimal power, and obtain a high S/N ratio or less noise and predominantly high sensitivity, because a single sensing switch can perform functions of more than one conventional apparatus.

Figure 7A:
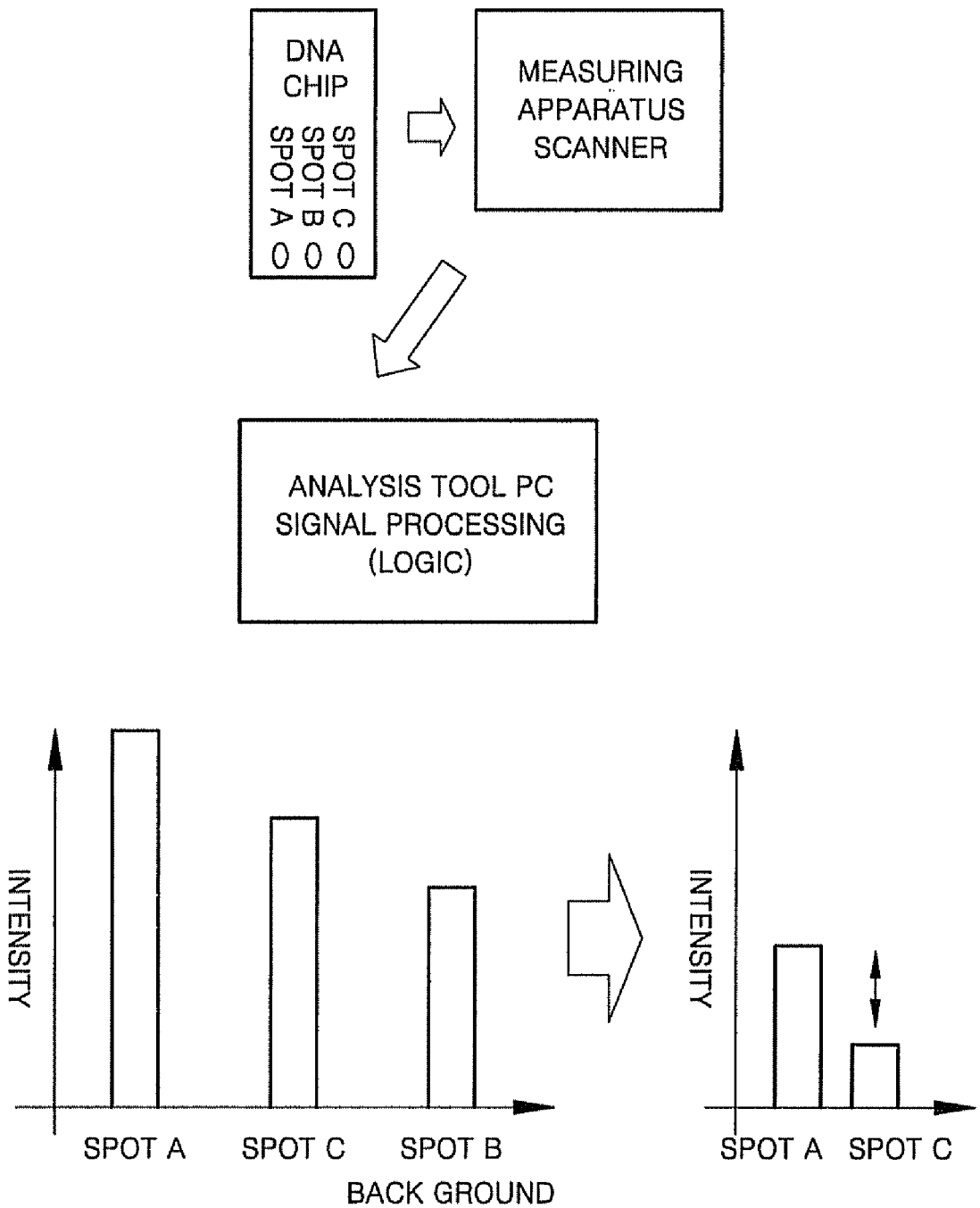
FIGS. 7A and 7B illustrate the analysis results obtained using the conventional differential sensing system shown in FIG. 6A.
Figure 7B:
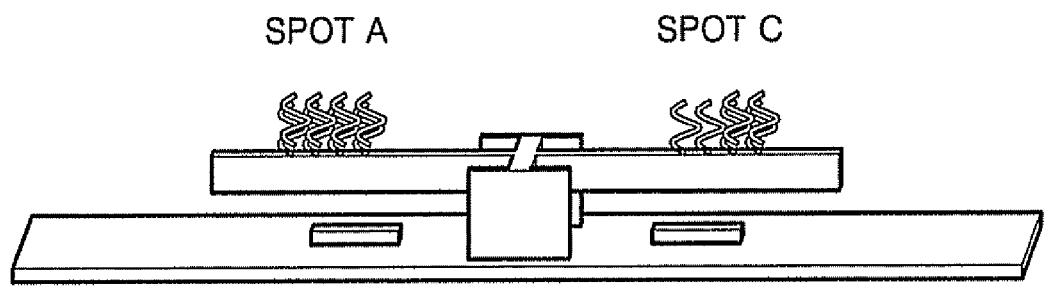

FIGS. 7A and 7B illustrate the analysis results obtained using the conventional differential sensing system shown in FIG. 6A. Referring to FIG. 7A illustrating a conventional method, in order to differentially sense the spots A, B, and C of the DNA chip, each of the spots A, B, and C is scanned and then the intensity of each spot is compensated by subtracting the intensity of the background spot B therefrom. As a result, differential intensities of the spot A and the spot C can be obtained. On the other hand, referring to FIG. 7B illustrating a sensing method according to an embodiment of the present invention, a single sensing switch compares the amounts of the receptors immobilized on the spot A and the spot C disposed on arms of a sensing plate by operating as a seesaw operates, so that the differential sensing of the spot A and the spot C can be directly performed without any production of a common noise due to spot B.

Figure 8A:
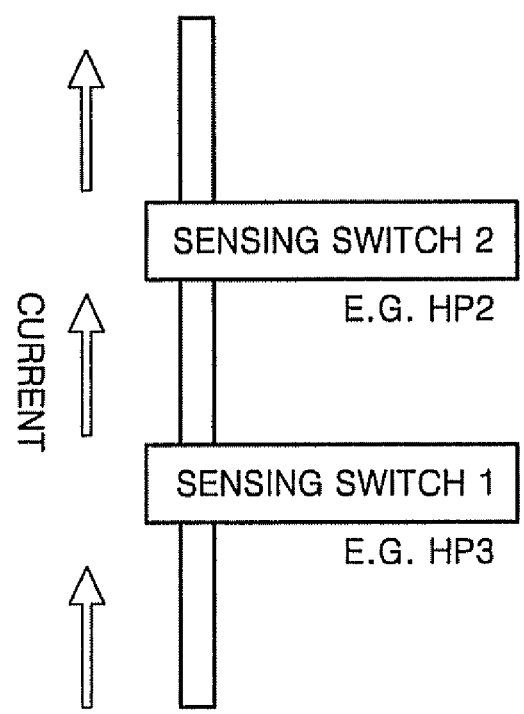
FIG. 8A illustrates an 'AND' logic sensing circuit according to an embodiment of the present invention.
Figure 8B:
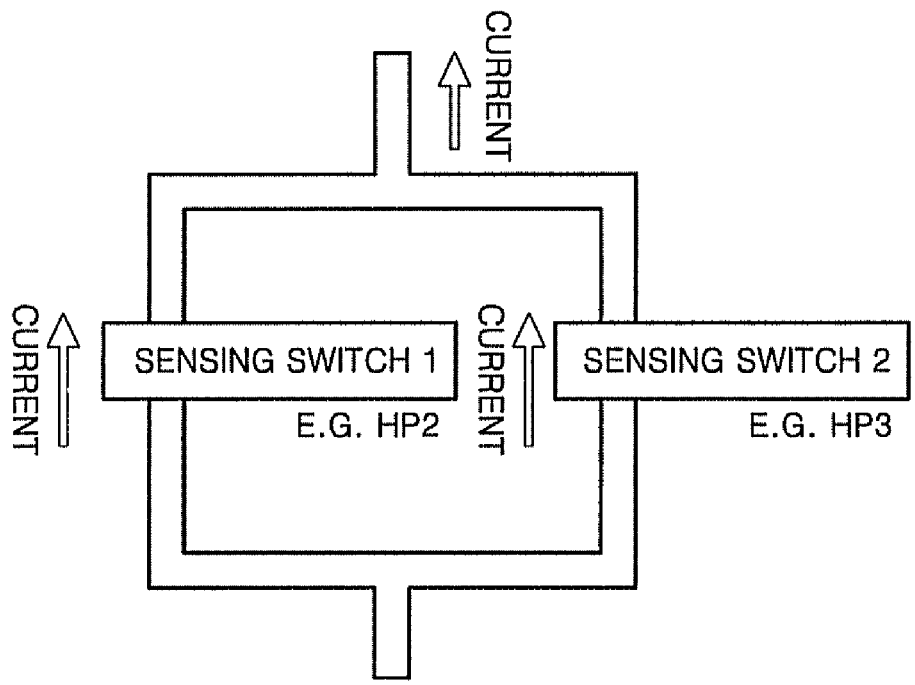
FIG. 8B illustrates an 'OR' logic sensing circuit according to an embodiment of the present invention.

FIG. 8A illustrates an 'AND' logic circuit of a sensing circuit according to an embodiment of the present invention, and FIG. 8B illustrates an 'OR' logic circuit of a sensing circuit according to an embodiment of the present invention. In the 'AND' logic circuit illustrated in FIG. 8A, when sensing switches 1 and 2 are turned on, for example, when the subject is infected by HP2 and HP3, the output of the circuit is activated. In the 'OR' logic circuit illustrated in FIG. 7B, when the sensing switch 1 closed or the sensing switch 2 closed, for example, when the subject is infected by HP2 or HP3, the output of the circuit is activated.

Figure 8C:
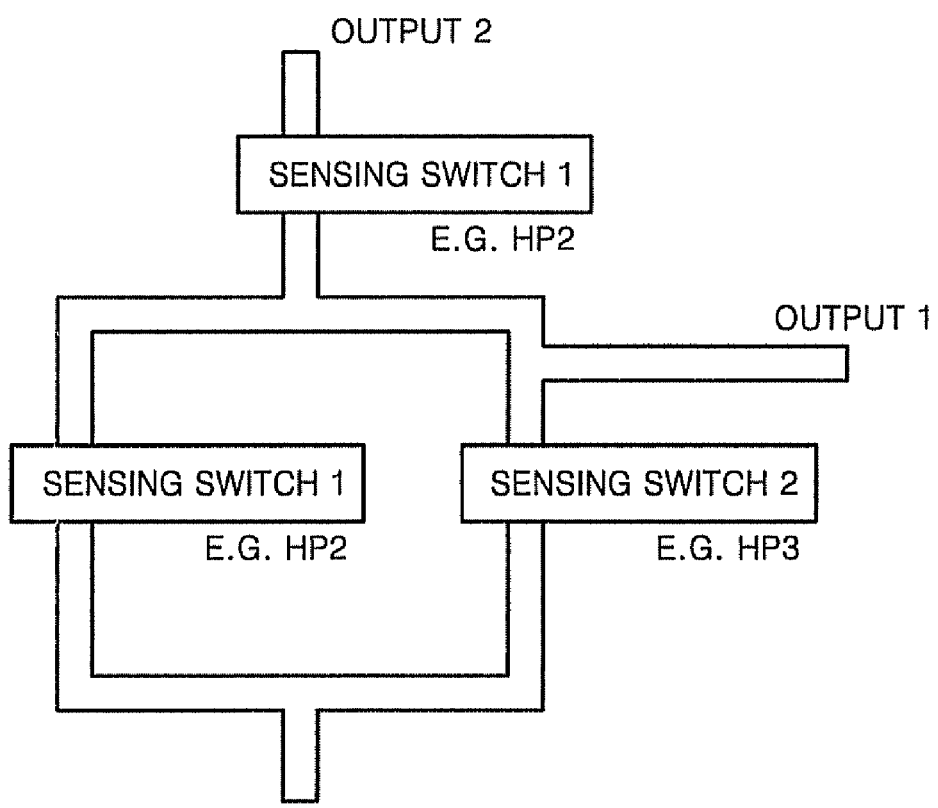
FIG. 8C illustrates a combined circuit including at least one 'AND' logic circuit and at least one 'OR' logic circuit.

FIG. 8C illustrates a combined circuit including at least one 'AND' logic circuit and at least one 'OR' logic circuit according to an embodiment of the present invention. HP2 and/or HP3 infection can be precisely sensed by measuring on (1) or off (2) at outputs 1 and 2. The results diagnosed from the output signals of FIG. 8C are shown in table 1.

TABLE 1

| Output | | | HP2 | HP3 |
|---|---|---|---|---|
| Output 1 | Output 2 | | Infection | Infection |
| 1 | 1 | => | ○ | ○ |
| 0 | 1 | | ○ | X |

TABLE 1-continued

| Output | | HP2 | HP3 |
|---|---|---|---|
| Output 1 | Output 2 | Infection | Infection |
| 1 | 0 | X | ○ |
| 0 | 0 | X | X |

The highly sensitive sensing logic circuit according to an embodiment of the present invention is a landmark design for a LOC and may replace a conventional device sensor (DNA chip)+Scanner/controller+analysis tool (PC).

As for a working principle for the sensing switch, four torques, each given by

Torque=Force×distance, affect the sensing plate. The four torques are:

1) an electrostatic or magnetic torque (Me) that derives the movement of the sensing plate and depends on the arrangement and geometry of electrodes or a magnetic field generation device, an electric or magnetic field, and the charge of a receptor, or a magnetic bead;

2) an inertial torque (I) that is proportional to angular acceleration and depends on the rotational inertia (I) of a rotating connecting beam;

3) a damping torque (D) that is proportional to a rotational speed and depends on a damping factor (F), such as medium's viscosity or sensor dimension; and.

4) a mechanical restoring torque (Mm) that is proportional to a tilting angle and depends on a material composing the sensor and geometry/design.

The relationship among the four-torques can be given by $$I\frac{d^2\theta}{dt^2} + F\frac{d\theta}{dt} + Mm(\theta) = Me(\theta) \quad (1)$$

Figure 9A:
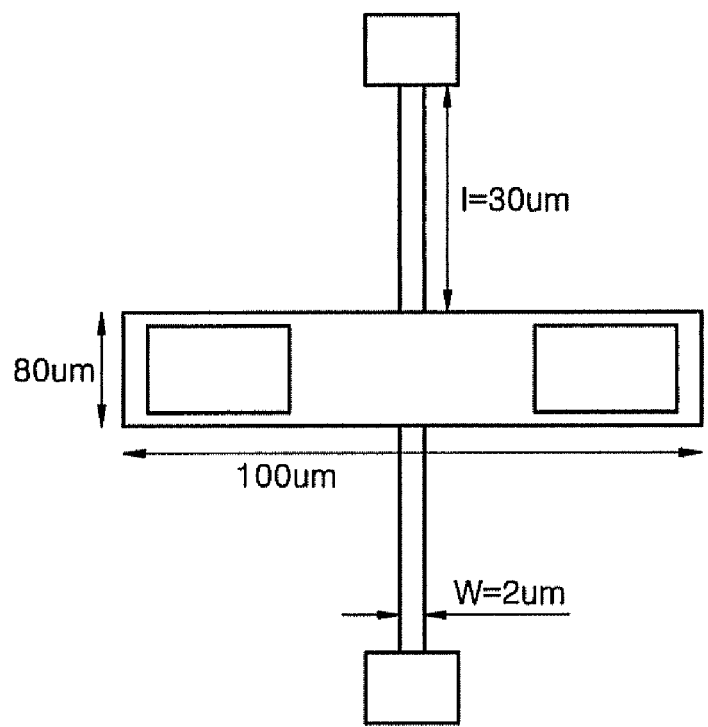
FIGS. 9A and 9B illustrate scales for measuring the torque of the sensing switch shown in FIG. 3.
Figure 9B:
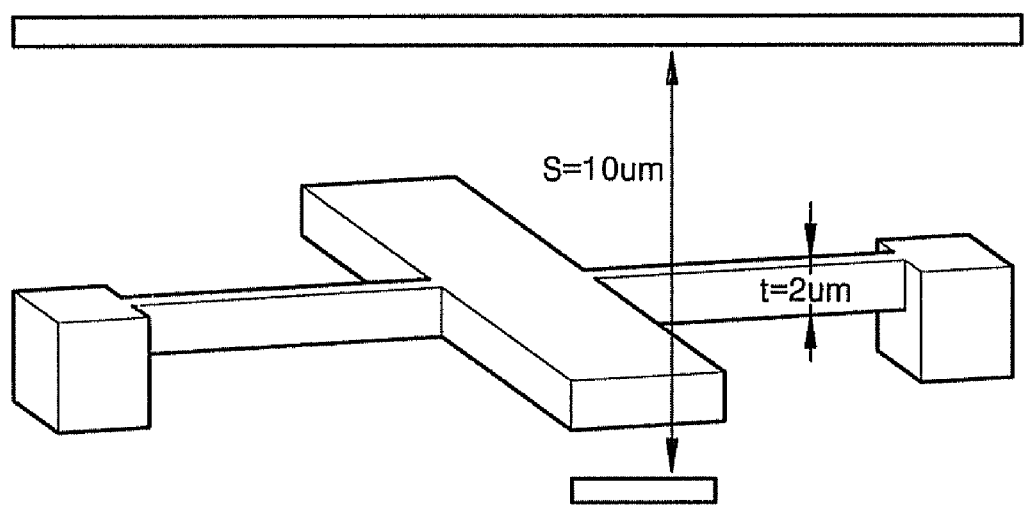

FIGS. 9A and 9B illustrate scales for measuring the torque of a sensing switch according to another embodiment of the present invention. The receptor binding region is 80×30 μm², the sensor is made of doped polysilicon, Young's modulus (E) for the sensor is 150 Gpa, poisson ratio (ν)=0.22 (for example), relative dielectric constant of a buffer ($\in_b$) is 50, and an applied voltage is 10V. Accordingly, in a steady state $$I\frac{d^2\theta}{dt^2} + F\frac{d\theta}{dt} + Mm(\theta) = Me(\theta) \quad (1)$$

$$\text{when } \frac{d\theta}{dt} = 0 \frac{d^2\theta}{dt^2} = 0, \quad (2)$$

and therefore, $Mm(\theta) = Me(\theta)$. (3)

As described above, a design parameter/requirement can be obtained using an analytical solution, and most of all, whether the sensing switch can operate or not can be confirmed. In order to obtain a dynamic response, such as a response speed of the sensor or the like, the equation (I) must be solved without setting dθ/dt or d'θ/dt² to 0. However, the obtaining of the dynamical response is not important at a time when feasibility of the sensor is considered.

The mechanical restoring torque is given by $$\text{Mechanical restoring torque} = \left(\frac{2KG}{l}\right)\theta \quad (4)$$

$$\text{where } K(\text{stiffness coeff. Of the beam}) = wt^3\left[\frac{1}{3} - 0.21\frac{t}{w}\left(1 - \frac{t^4}{12w^4}\right)\right] \quad (5)$$

$$\text{and } G(\text{elastic modulus of the beam in shear}) = \frac{E}{2(1+v)} \quad (6)$$

(See B. R. Hopkins, *design analysis of shafts and beams* 2nd edition).

As a result, K (Stiffness coeff. Of the beam) is 2.25×10⁻²⁴ m⁴, G (elastic modulus of the beam in shear) is 61.47×10⁹ N/m², and the restoring torque is 9.22×10⁻⁹ Nm.

The electrostatic torque is be given by

Me(θ)=Fe×distance, where $$Fe = qE = \frac{qV}{S\varepsilon_b} \quad (7)$$

The present invention will be described in detail with reference to the following Examples. These examples are for illustrative purposes only and should not be construed as limiting the scope of the present invention.

EXAMPLE 1

Torque was measured using the sensing switch illustrated in FIGS. 9A and 9B under the following condition: 80% non-specific binding to mismatched receptor (single mismatch receptor, hypothetically); immobilized 25mer receptor DNA density of 2×10¹² molecules/cm²; 100% hybridization with perfect matched DNA (25mer); a receptor of 5' SH-C6-AGATCAGTGCGTCTGTACTAGCACA 3' (See A. Peterson, *the effect of surface receptor density on DNA hybridization*, Nucleic Acid Research 2001, 29, 24, pp 5163-5168).

The results of steady state analysis are described below.

Total effective charge (q)=reactive surface area×molecules/area×number of electrons/molecule×charge/electron=6×10⁻¹¹ C;

the electric field=10V/(50× um)=2×10⁵ N/C; and

Fe=1.2×10⁻⁵ N.

Accordingly, as described below, the sensor did not operate because the electrostatic torque, was smaller than the mechanical restoring torque.

Electrostatic Torque=Fe×40 μm=4.8×10⁻¹⁰ Nm

Restoring torque=9.22×10⁻⁹ Nm

Some design/experimental tweaking was made in Example 1 and the following different results were obtained.

First, in a first alteration, the applied voltage was 200V.

Electrostatic torque=9.6×10⁻⁹ Nm>9.22×10⁻⁹ Nm (Restoring torque).

Electrodes including an oxide insulating layer were assumed to interrupt hydrolysis. In theory, the voltage can be increased to a dielectric breakdown voltage (Oxide>10 MV/cm, liquid of about 1 MV/cm). In the present embodiment, the dielectric break down voltage of the liquid was about 1000V/10 um. The increase in the voltage resulted in the electrostatic torque being greater than the mechanical restoring torque, and thus the switch operated.

In a second alteration, effective charges were increased using RCA. Hence, 100 times rolling multiplication (few minutes) and the electrostatic torque ($48 \times 10^{-9}$ Nm) was larger than the mechanical restoring torque ($9.22 \times 10^{-9}$ Nm)

Electrostatic Torque=$48 \times 10^{-9}$ Nm>$9.22 \times 10^{-9}$ Nm (Restoring torque)

In a third alteration, beam designs and materials were modified. In this case, a lower young's modulus and a longer beam length was used. As a result, the mechanical restoring torque was smaller than the electrostatic torque and thus the switch was able to operate.

EXAMPLE 2

Figure 10:
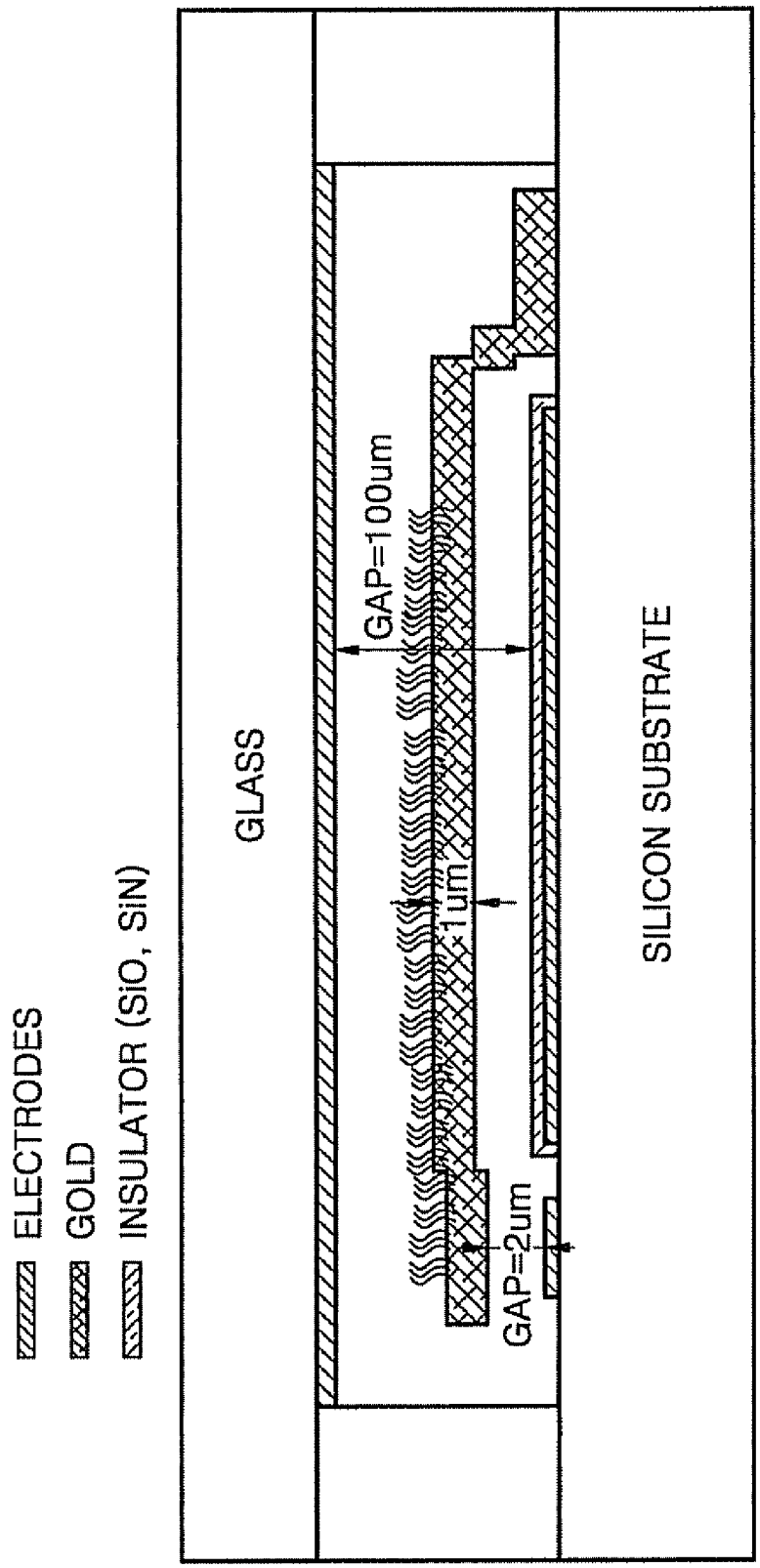
FIG. 10 is a schematic view of an apparatus that is used to simulate a sensing switch according to an embodiment of the present invention.
Figure 11A:
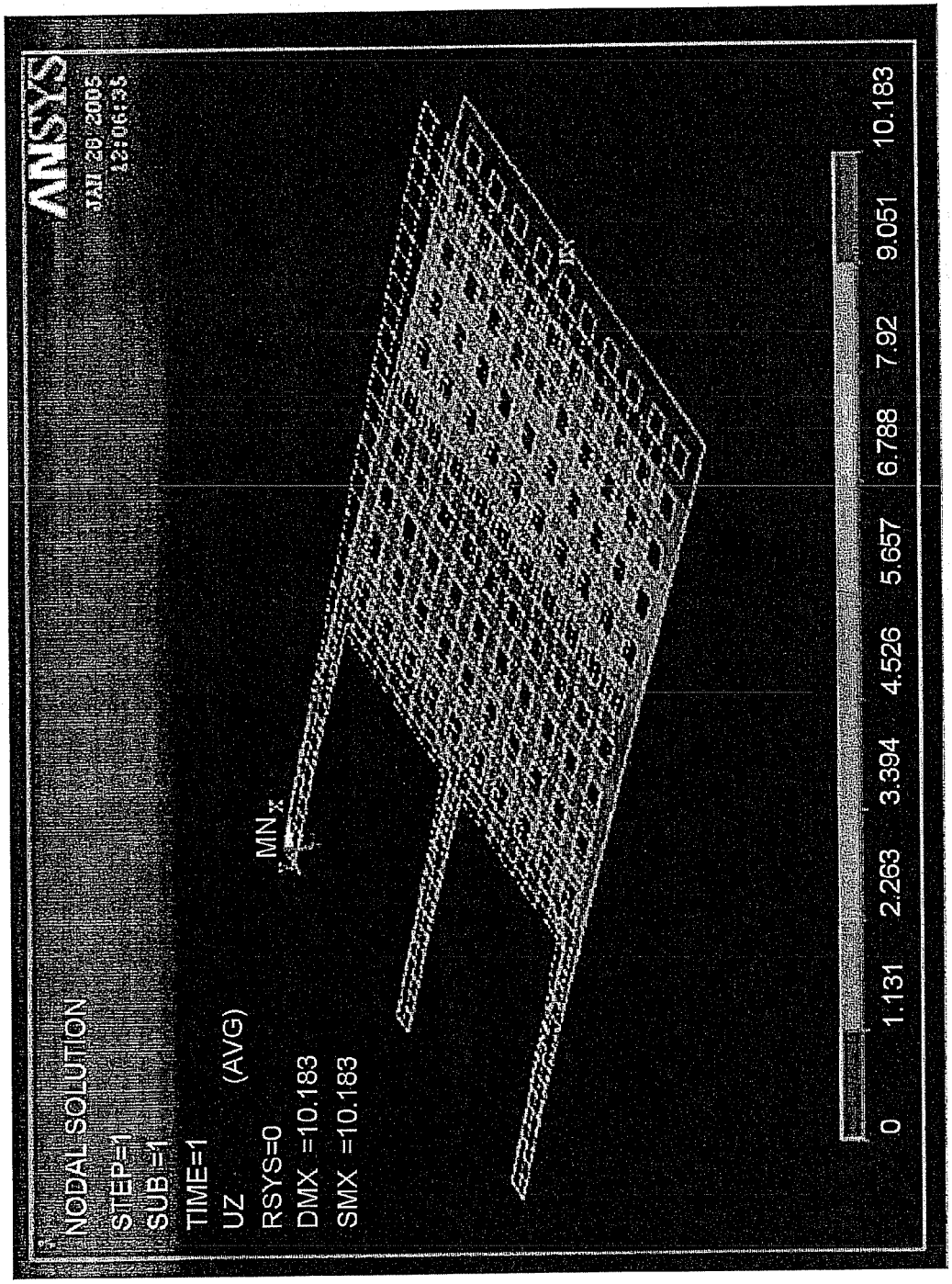
FIGS. 11A, 11B, 11C and 11D illustrate the results of a simulation of the sensing switch according to an embodiment of the present invention.
Figure 11B:
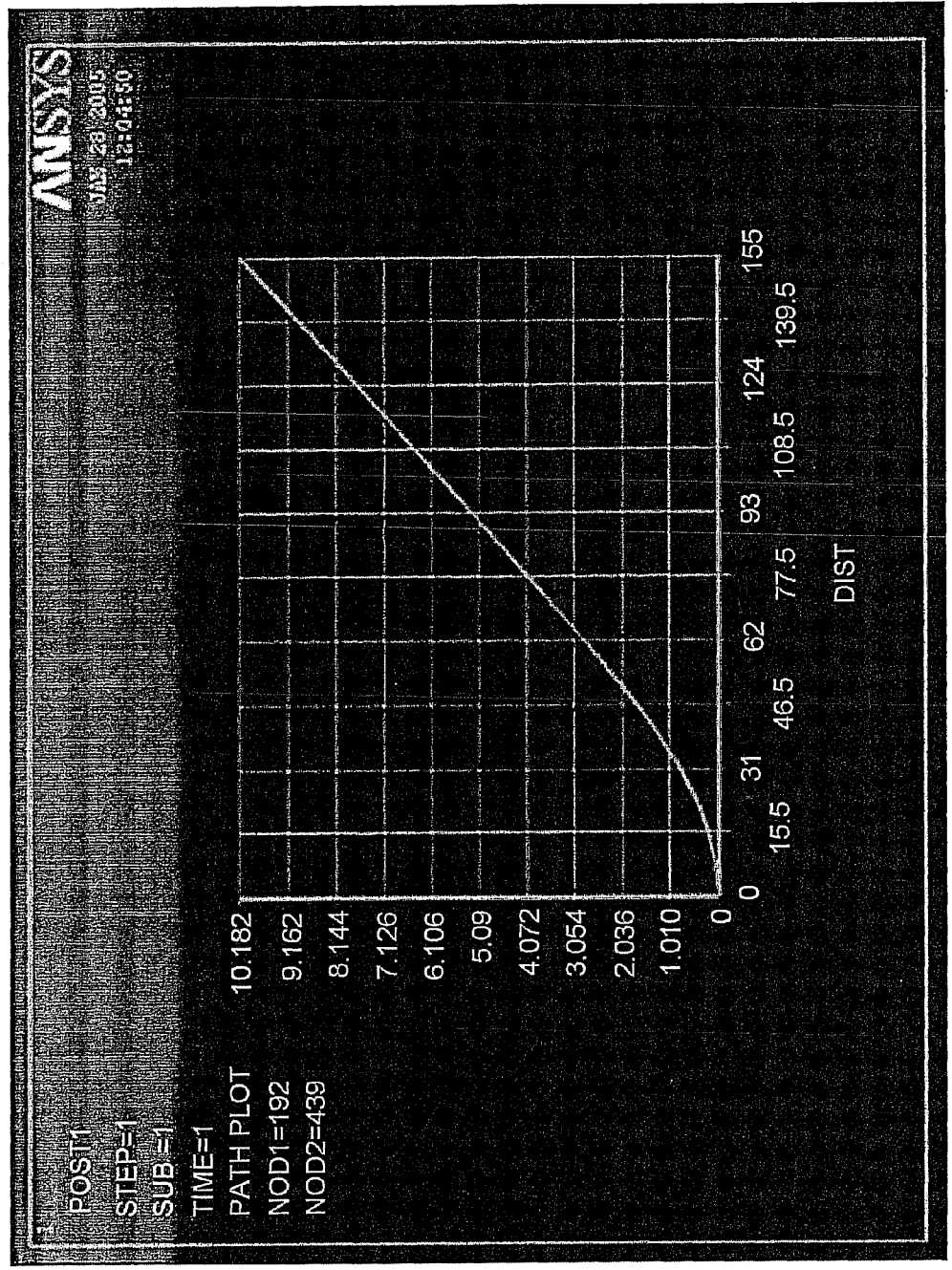
Figure 11C:
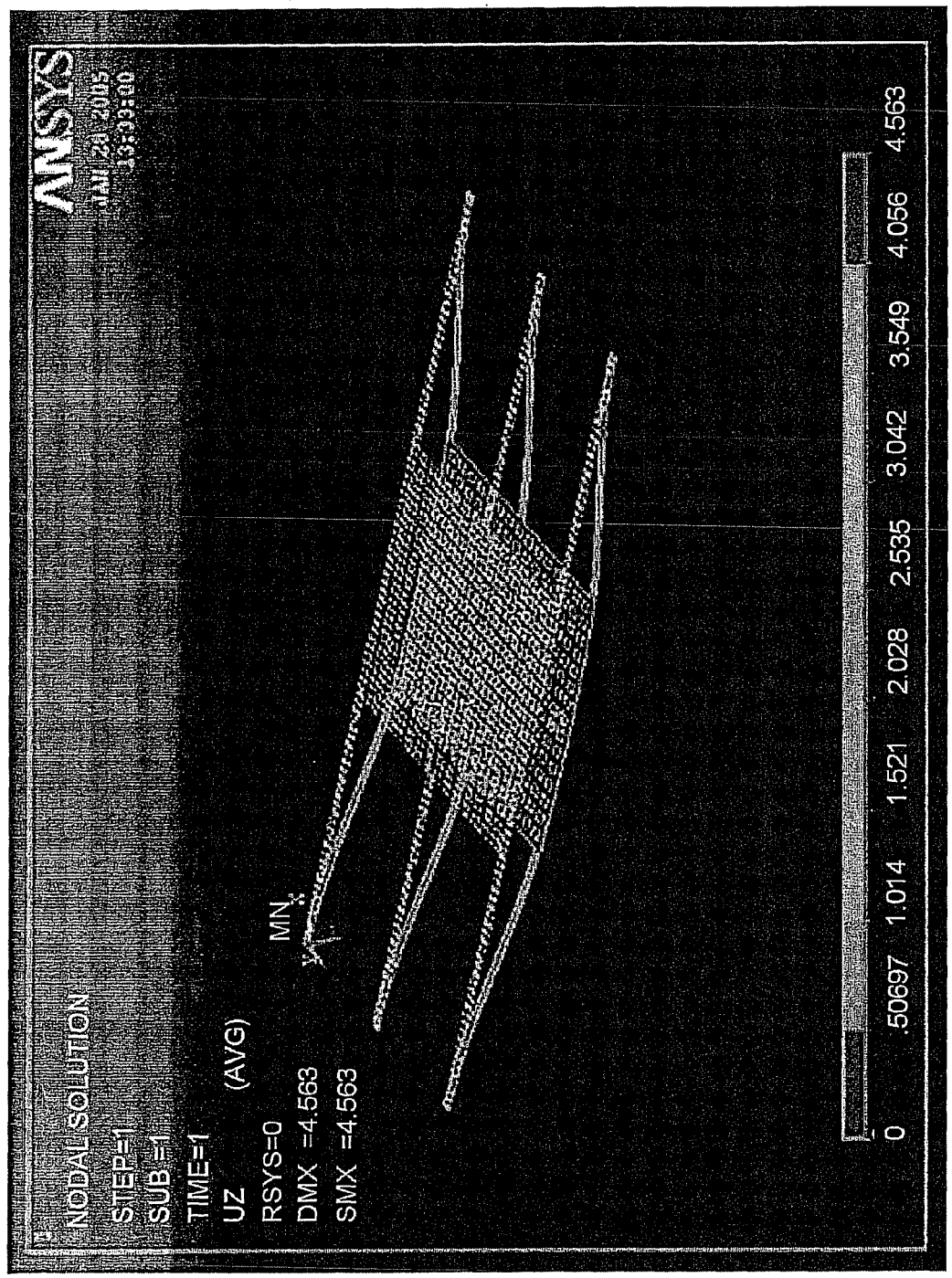
Figure 11D:
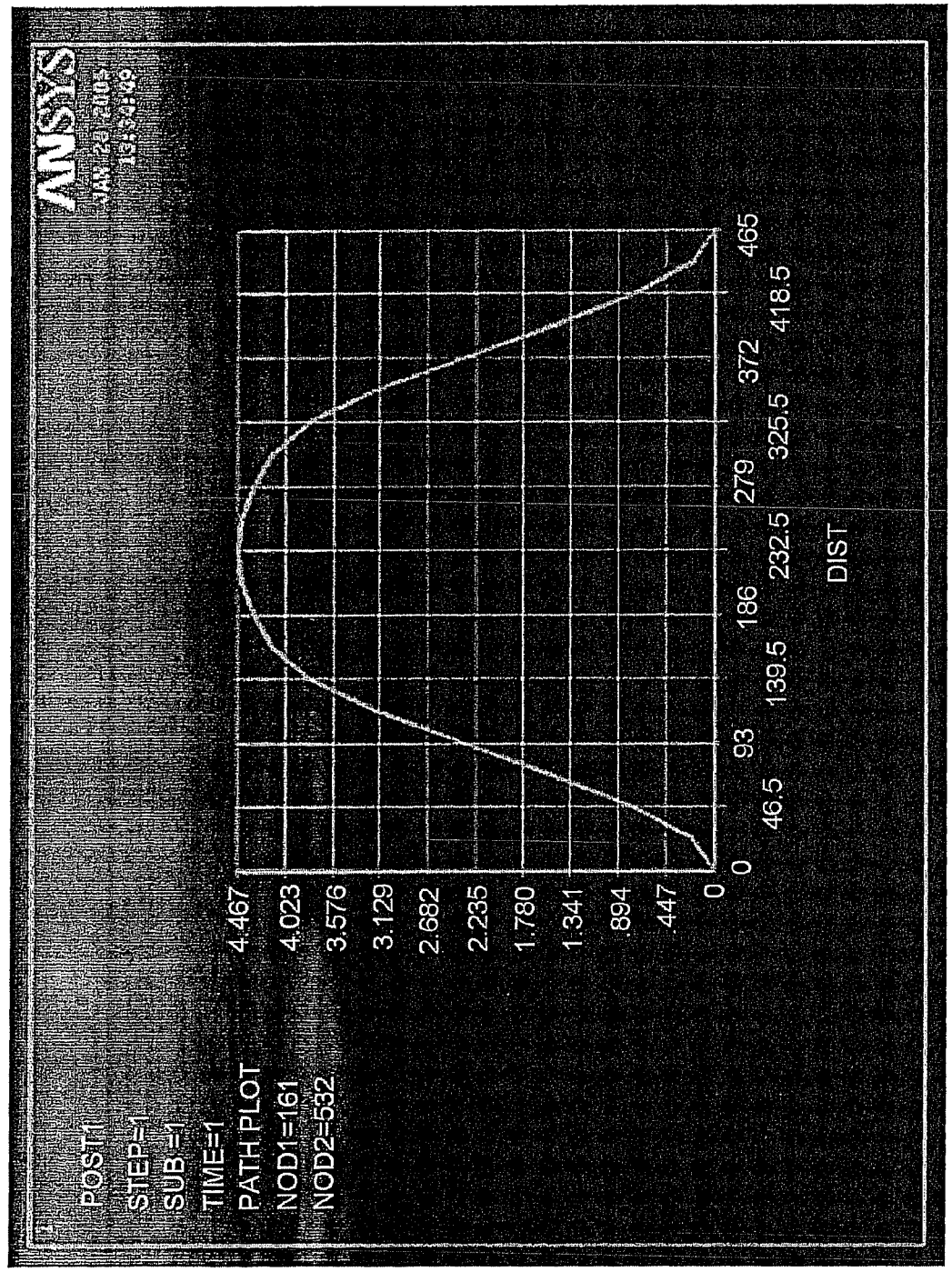

In order to confirm whether the sensing switch shown in FIG. 10 can act as a switch, a simulation experiment was conducted in which a nucleic acid used as biomolecule was sensed using the apparatus illustrated in FIG. 9. (See A. Peterson, *the effect of surface receptor density on DNA hybridization*, Nucleic Acid Research 2001, 29, 24, pp 5163-5168). ANSYS 8.0 (obtained from ANSYS, Inc., USA) was used as a simulation program, a shell 93 (suited for large deflection) was used as an element, a beam was made of gold, young's modulus was 75 GPa (silicon ~169 GPa), poisson's ratio was 0.42, a density was $1.932 \times 10^4$ kg/m3 (silicon ~2.33e3 kg/m3), the beam had a thickness of 1 µm, the relative permittivity of a buffer solution was 80, a gap between two electrodes was 100 µm, an applied potential was 10 V, an immobilized 25mer receptor DNA density was $2 \times 10^{12}$ molecules/cm$^2$, 100% hybridization with perfectly matched DNA (25mer) was performed, and a receptor used was 5' SH—C6-AGATCAGTGCGTCTGTACTAGCACA 3'. Different designs as indicated in Table 2 were adopted. The simulation results are shown in FIGS. 11A (three beams) and 11B (six beams). (Etch hole was 5 µm×5 µm, Distance between holes: 5 µm). Referring to FIGS. 10A and 10B, the beam is bent enough to connect two electrodes in both cases, thus acting as a switch.

TABLE 2

| # of beams | beam, length | beam width | square plate length | deflection |
|---|---|---|---|---|
| 3 | 50 um | 5 um | 105 um | 10 um |
| 6 | 155 um | 5 um | 155 um | 4.4 um |

EXAMPLE 3

A force generated between the magnetic bead and the magnetic generation device that was sufficiently strong to move a switch but not greater than a binging force between the receptor and the ligand was measured using the sensing switch shown in FIG. 2

A BioMag® BM551 was used as the magnetic bead. Streptavidin as a ligand was bound to the surface of the magnetic bead. A neodium magnet was used as the magnetic field generation device. The magnetic bead and the neodium magnet had the following characteristics: Br=1.22 Tesla, $\mu_0 = 1.26 \times 10^{-6}$ H/m, magnetic mass susceptibility=$2.54 \times 10^{-3}$ m$^3$/kg, density=$1.70 \times 10^3$ kg/m$^3$, magnetic susceptibility=4.31, bead diameter=$1.50 \times 10^{-6}$ m, V=$1.77 \times 10^{-18}$ m$^3$, and L_magnet=0.003 m.

The magnetic force with respect to the distance between the magnetic bead and the magnetic filed generation device was measured using the values above and Formula 8.

$$F_{mag} = \frac{V\chi_m}{\mu_0}(\vec{B} \cdot \nabla)\vec{B} = \frac{V\chi_m}{2\mu_0} \nabla\left(|\vec{B}|^2\right) \qquad (8)$$

$$B_x = \frac{B_r}{2}\left[\frac{L+x}{\sqrt{R^2+(L+x)^2}} - \frac{x}{\sqrt{R^2+x^2}}\right]$$

Figure 12:
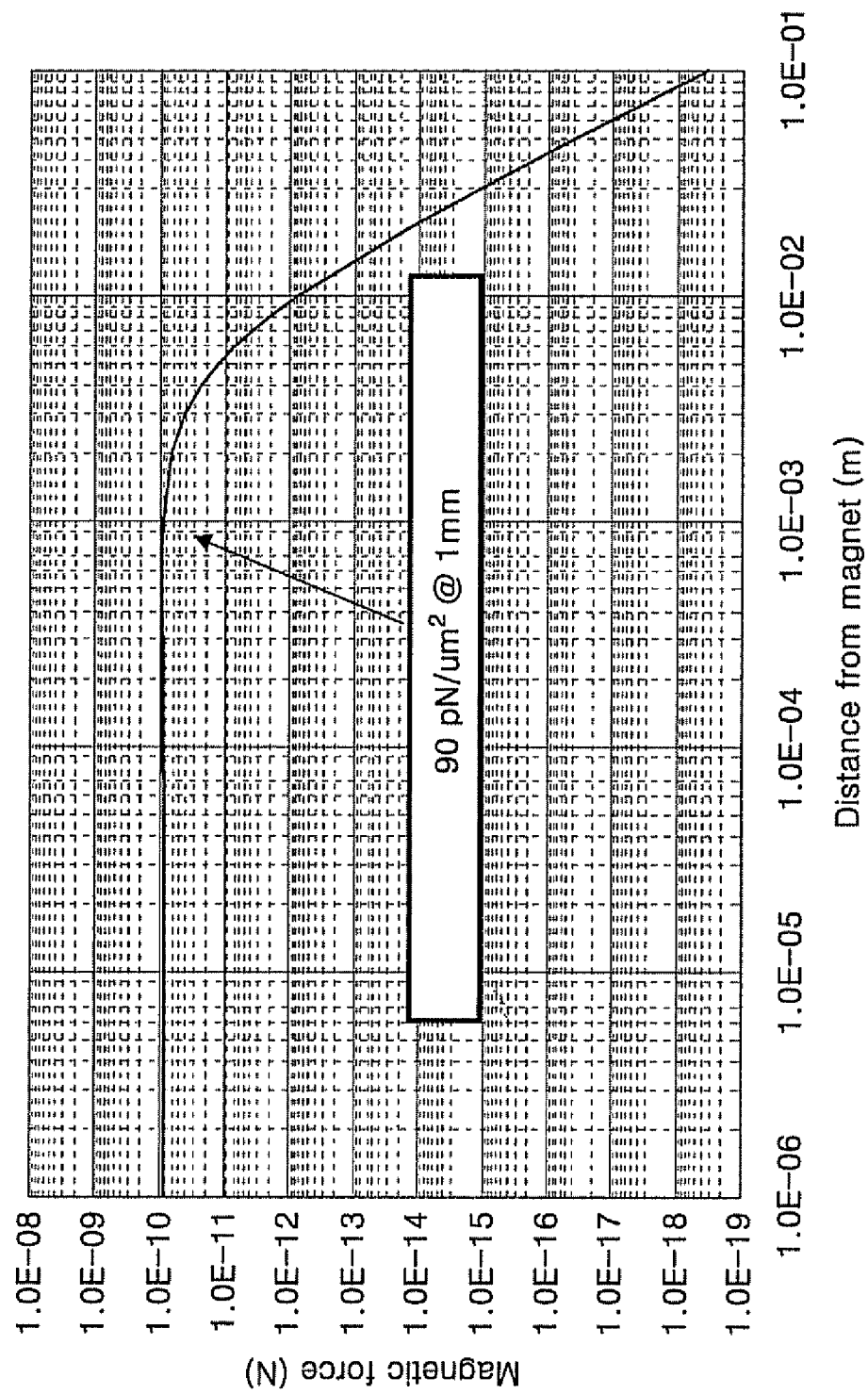
FIG. 12 is a graph of a magnetic force with respect to a distance between a magnetic bead and a magnetic field generation device of the sensing switch shown in FIG. 2.

The results are shown in FIG. 12. Referring to 12, the magnetic force between the magnetic bead and the magnetic filed generation device was 90 pN when they were separated by 1 mm.

Meanwhile, in general, the known mutual binding force between streptavidin and biotin is 260±20 pN (See Proc. IEEE 85(4), 672-680, 1997).

From the results, it was found that in the sensing switch according to an embodiment of the present invention, the magnetic force (90 pN) generated between the magnetic bead and the magnetic filed generation device was strong enough to move the sensing switch but smaller than a binding force (260±20 pN) of the receptor-ligand so as not to interrupt the binding between the receptor and the ligand.

EXAMPLE 4

Figure 13A:
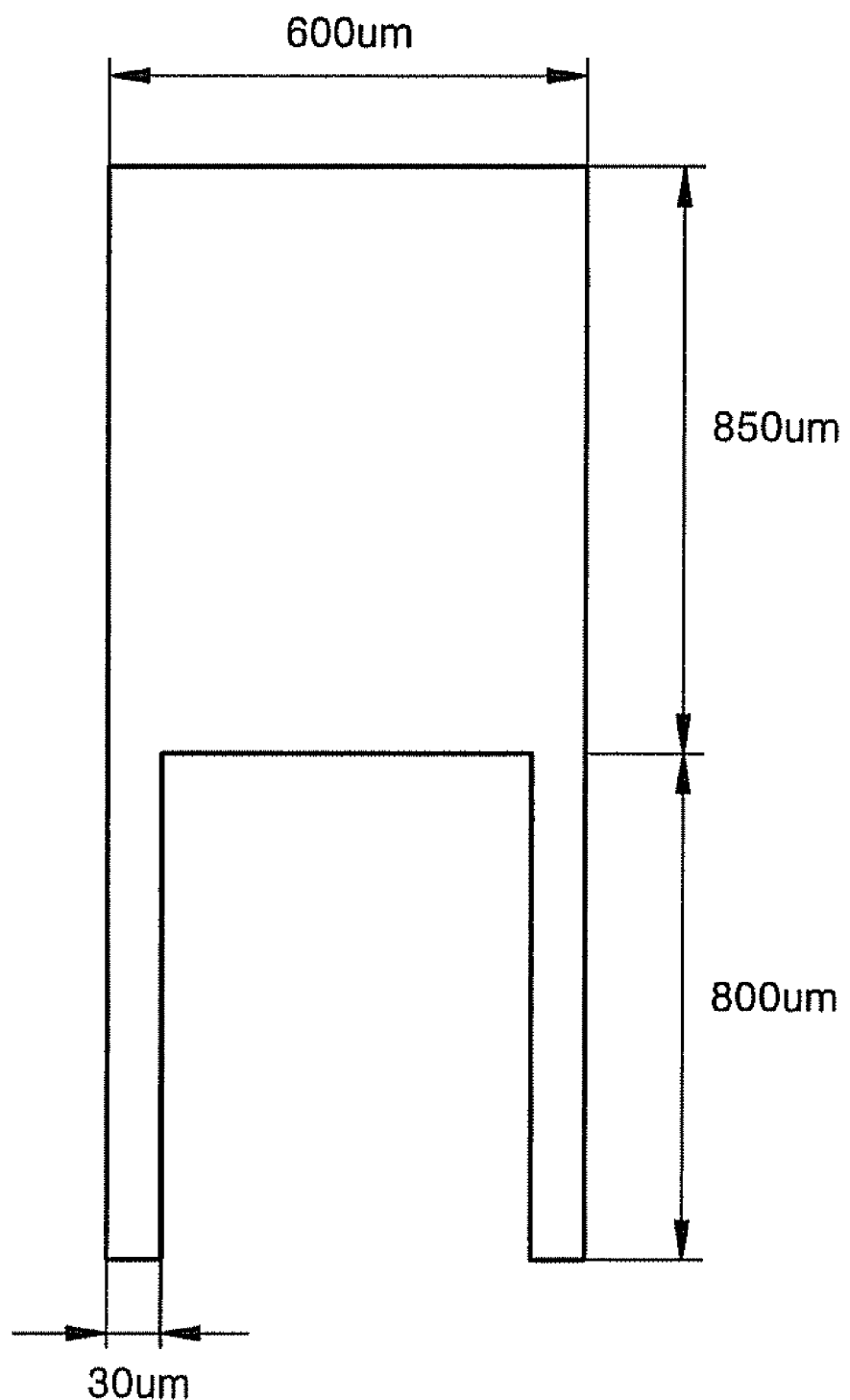
FIG. 13A illustrates a scale of a sensing plate that is used in a simulation of the sensing switch shown in FIG. 2.

A simulation was performed to determine that the sensing switch shown in FIG. 2 acted as a switch in the same manner as in Example 2. FIG. 13A illustrates the dimensions of a sensing plate that is used in a simulation of the sensing switch shown in FIG. 2. The sensing plate was formed of silicon single crystal (Young's modulus =169 GPa, Density=2330 kg/m$^3$) and had a thickness of 3 µm.

Figure 13B:
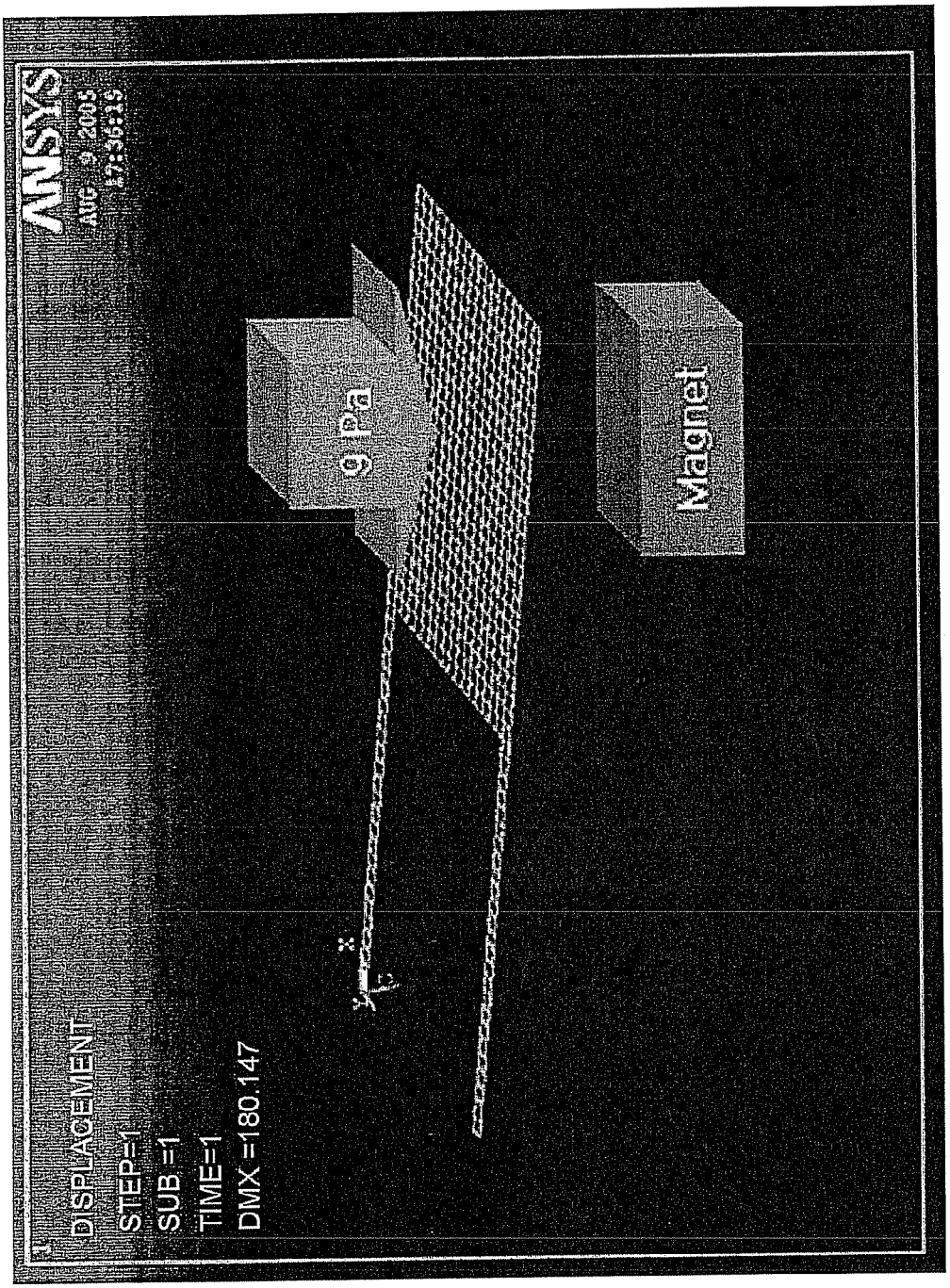
FIGS. 13B, 13C and 13D illustrate the result of a simulation performed using the sensing plate shown in FIG. 13A.

Under these conditions, the measured pressure was 0.1×90 N/m$^2$=9 Pa. Under such a pressure, a distance between the sensing plate and the switching electrode at which the sensing plate could be sufficiently bent to connect a pair of switching electrodes was measured. In this case, it was assumed that the magnetic bead was bound to 10% of the cross-sectional surface of the sensing plate. FIG. 13B shows the results of simulation.

From the results, the allowable distance between the sensing plate and the switching electrodes was determined to be 180 µm or less. Within this range, the sensing plate was able to contact the switching electrodes when an electric field was applied.

Figure 13C:
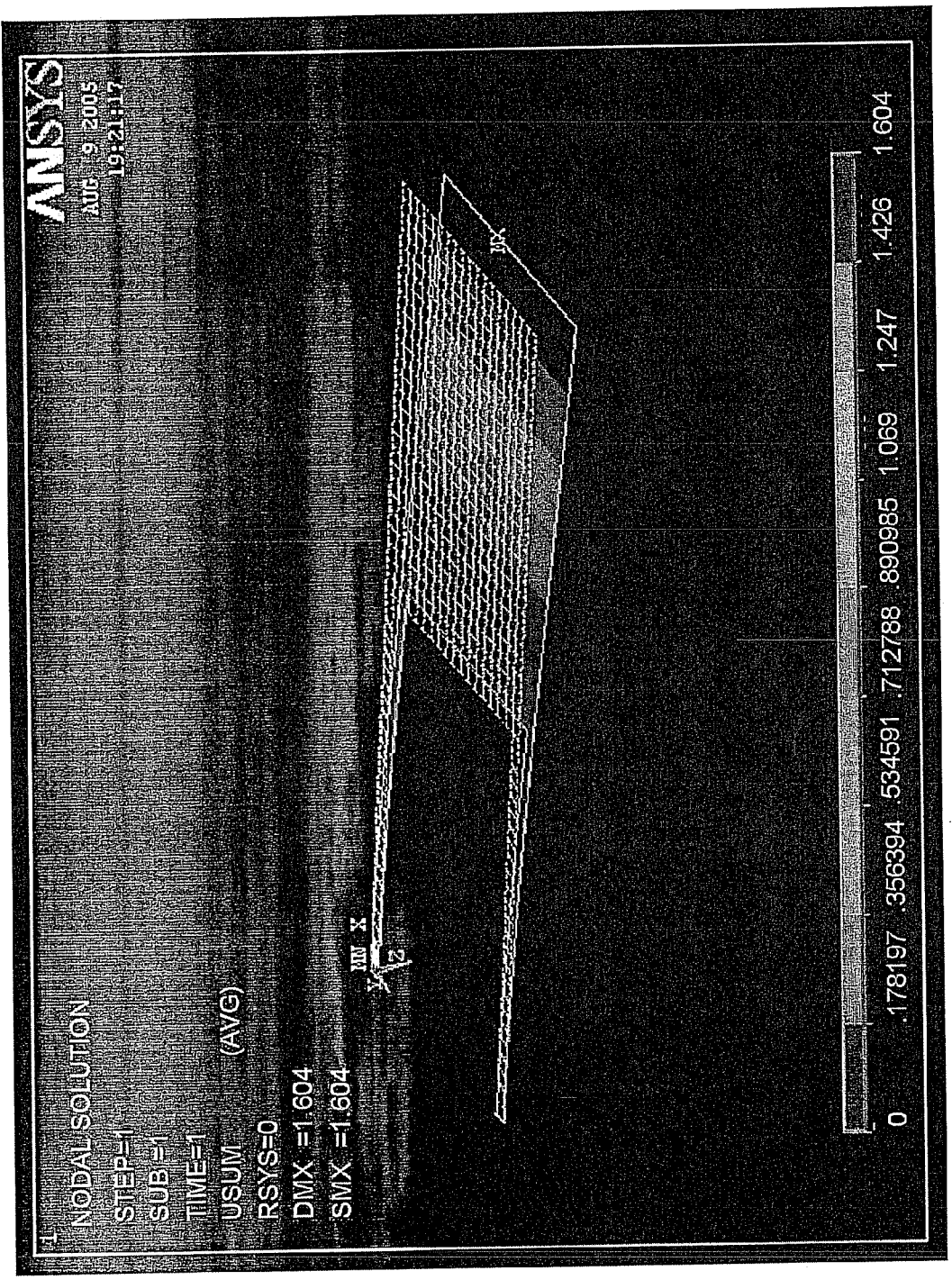
Figure 13D:
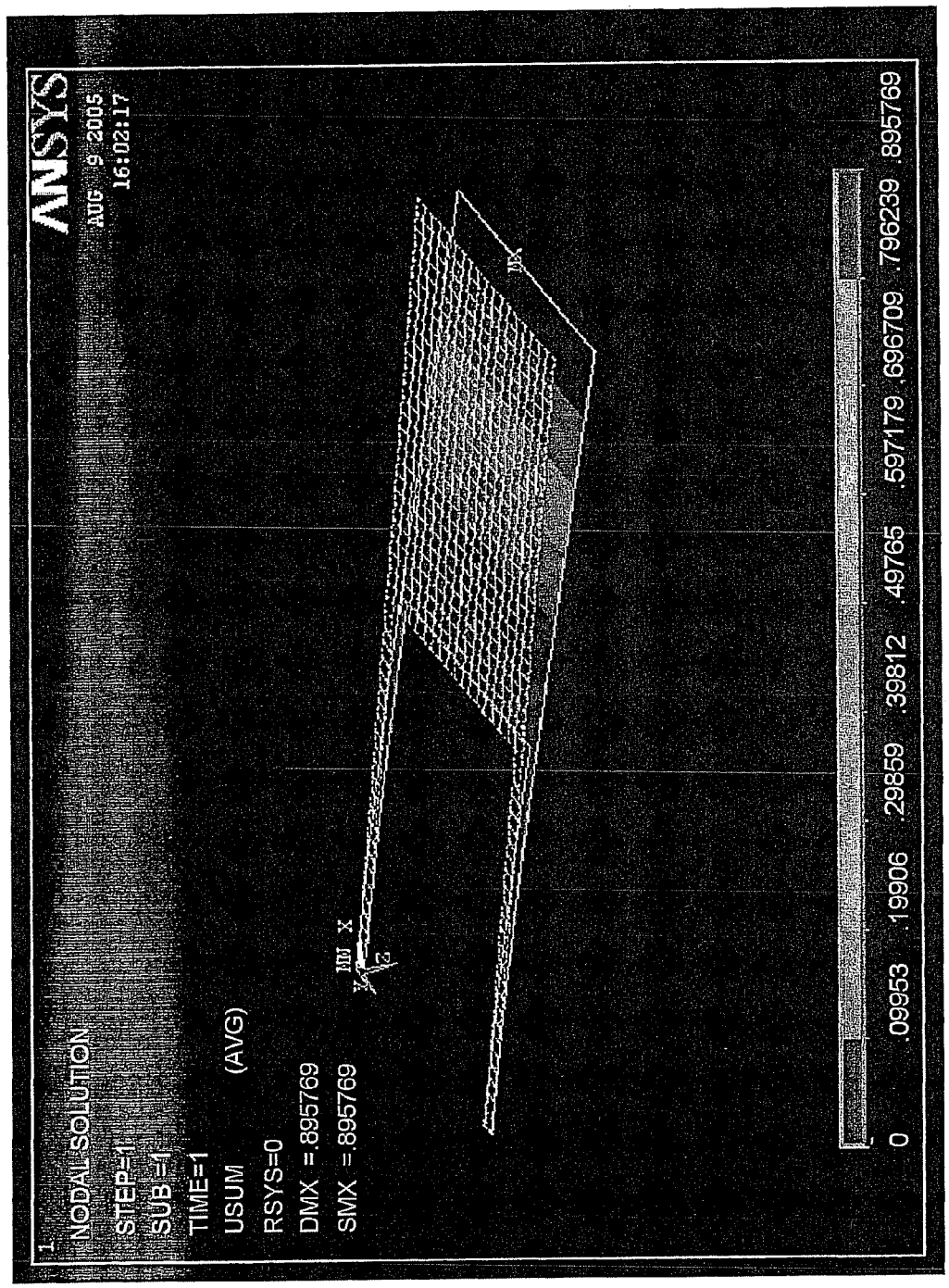

In addition, it was determined whether the sensing plate bent due to the weight of the sensing plate and the magnetic bead such that the sensing plate contacted the switching electrodes even when an electric filed was not applied. In this case, it was assumed that the magnetic bead was bound to the entire cross-sectional surface of the sensing plate. FIG. 13C illustrates the results of the simulation.

From the results, it was determined that, when a magnetic field was not applied, a distance required to maintain the separation of the sensing plate and the switching electrodes was 1.6 µm or greater.

That is, when the sensing plate was separated from the switching electrodes by 1.6-180 µm, the sensing switch could act as a, switch.

EXAMPLE 5

The sensing switch according to an embodiment of the present invention shown in FIG. 2 was manufactured using a semiconductor processing technique.

Figure 14:
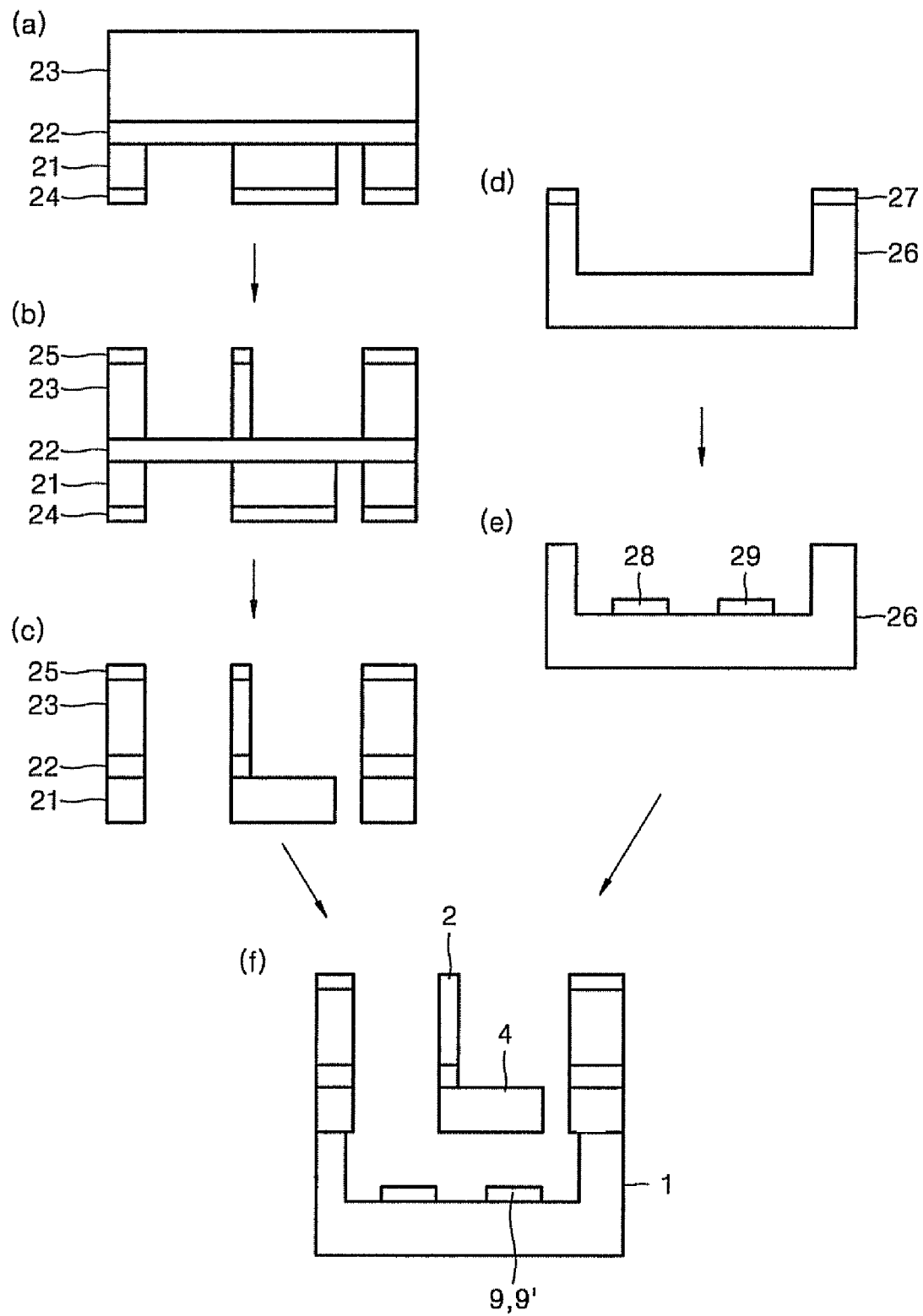
FIG. 14 schematically illustrates a method of manufacturing the sensing switch shown in FIG. 2.

FIG. 14 schematically illustrates a method of manufacturing the sensing switch shown in FIG. 2.

Referring to FIG. 14, in order to manufacture a sensing plate, first, an oxide layer 22 and a SOI wafer 23 were sequentially formed on a SOI wafer 21. The surface of the SOI wafer 21 was coated with a PR 24 and was etched using a conventional method using a first mask (operation a). Then, the SOI wafer 23 located opposite to the SOI wafer 21 was coated with a PR 25 and etched using a conventional method using a second mask (operation b). Next, the exposed oxide layer 22 was etched toward the SOI wafer 23 to manufacture a sensing plate (operation c).

Then, an oxide layer 26 was coated with poly-Si 27 and etched using a third mask (operation d). The resulting structure was patterned using a fourth mask, thus forming a pair of switching electrodes 29 and a contact pad connected to the switching electrodes 29 (operation e).

The resulting patterned structure was coupled with the sensing switch (operation f). The sensing switch illustrated in operation f of FIG. 14 corresponds to the sensing switch of FIG. 2, and corresponding elements have the same reference numerals in the operation f of FIG. 14 and FIG. 2.

Figure 15A:
FIGS. 15A and 15B are magnified scanning electron microscopy (SEM) images of a sensing switch manufactured using the method illustrated in FIG. 14.
Figure 15B:
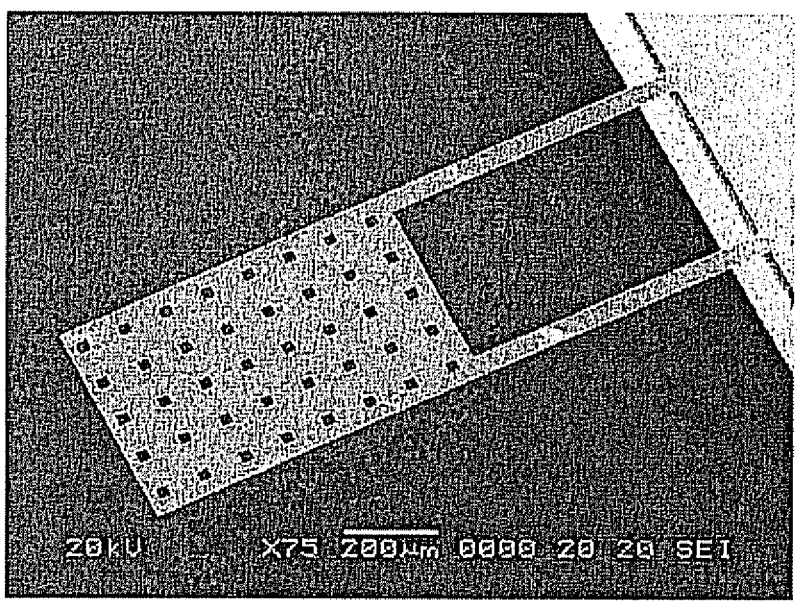

FIGS. 15A and 15B are magnified scanning electron microscopy (SEM) images of a sensing switch manufactured using the method illustrated in FIG. 14.

EXAMPLE 6

It was determined whether the sensing switch manufactured in Example 5 acted as a sensor.

A BioMag® BM551 was used as a magnetic bead. Streptavidin was bound to the surface of the magnetic bead. A neodium magnet was used as a magnetic field generation device. A direct current voltage of 1 V was applied to pair of switching electrodes.

Two experiments were performed: when biotin was immobilized on a receptor binding region on an upper surface of an end of the sensing plate; and when biotin was not immobilized.

Figure 16:
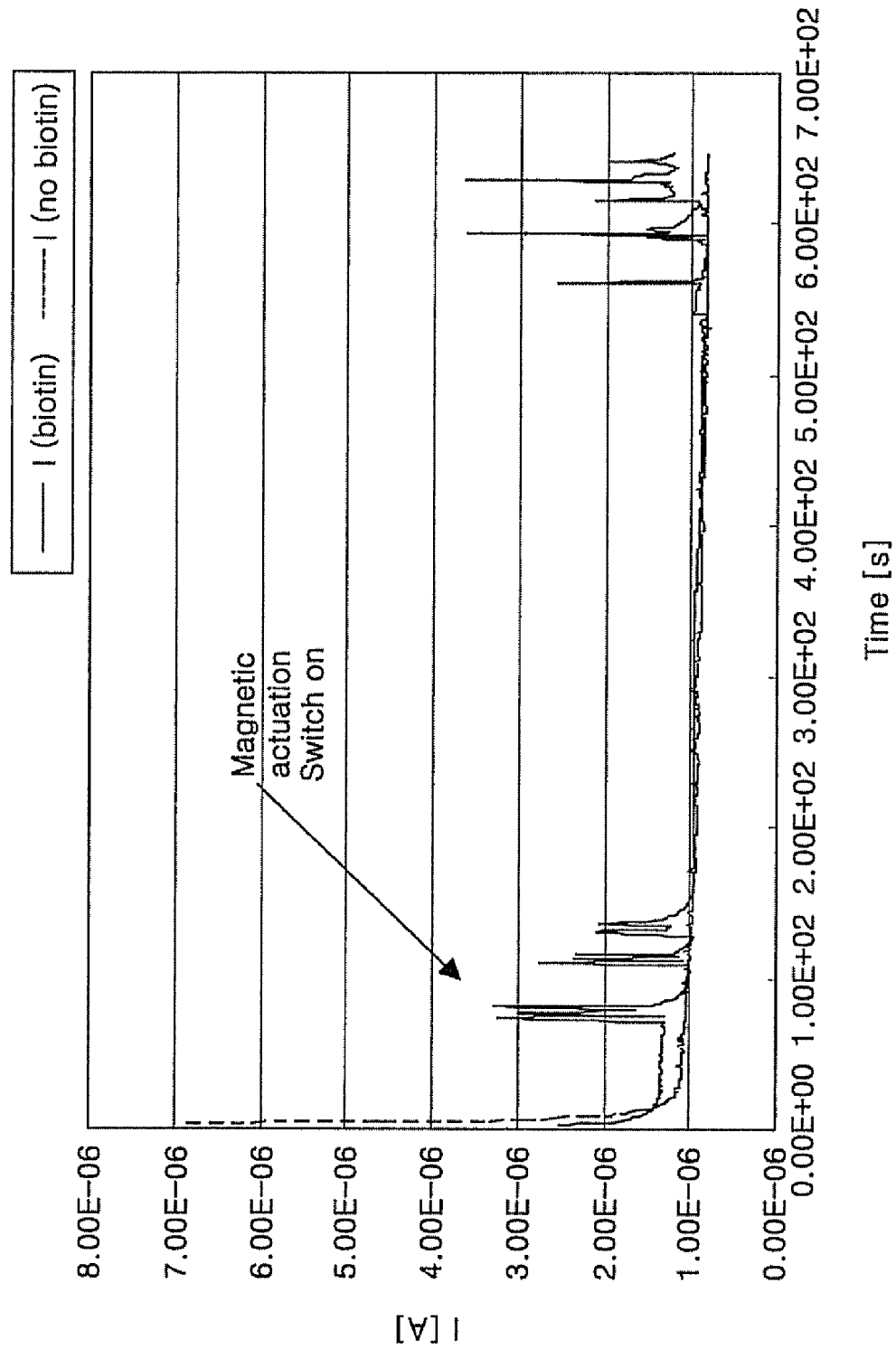
FIG. 16 shows sensing results indicating that the sensing switch shown in FIG. 15 effectively senses a receptor.

The results are shown in FIG. 16. Referring to FIG. 16, it was found that when biotin was immobilized on the receptor binding region of the sensing plate and a magnetic filed was applied, a current flowed. However, when biotin was not immobilized on the receptor binding region, a current did not flow. That is, the sensing switch according to an embodiment of the present invention was effectively able to sense a receptor.

As described above, according to the present invention, a target material, such as a biomolecule or chemical material, does not need to be labeled, signal processing for processing a fluorescent or electric detection signal using an analysis apparatus to process a fluorescent or electrical detection signal is not required, and a signal can be directly decoded by confirming whether a current flows according to whether a switch is opened or closed. That is, a sensing switch according to the present invention is more convenient than a conventional sensing switch because mechanical sensing and electrical switching can be performed at the same time, while conventionally, after the sensing, an acquired signal must be processed. In addition, minimal circuitry and power are required in the present invention, and thus the sensing switch can be miniaturized than conventional sensing methods that have been developed, that is, the sensing and signal processing. In addition, the sensing switch has minimal circuit noise, such as flicker and white noise, and the noise can be reduced by eliminating connection noise between a sensor and a post processor since a post processor is not required.

While the present invention has been particularly shown and described with reference to exemplary embodiments thereof, it will be understood by those of ordinary skill in the art that various changes in form and details may be made therein without departing from the spirit and scope of the present invention as defined by the following claims.

---

---

What is claimed is:

1. A sensing switch comprising:
   a substrate;
   a supporter on the substrate;

a sensing plate that is connected to a side of the supporter, is disposed parallel to and separated a predetermined distance from the substrate, and has a receptor binding region on an upper surface of an end portion thereof;

an electric or magnetic field generation device that induces deflection of the sensing plate when a receptor bound to the receptor binding region is selectively bound to an electrically or magnetically active ligand; and a pair of switching electrodes that are separated by a predetermined distance and are connected when the sensing plate contacts the substrate due to the deflection of the sensing plate.

2. The sensing switch of claim 1, wherein the ligand is a nucleotide, a protein, peptide, an antibody, an antigen, a polymer, or a liquid or vapor chemical agent, and is selectively bound to the receptor.

3. The sensing switch of claim 1, further comprising a connecting beam which connects two supporters formed on the substrate, wherein the sensing plate extends in opposite directions from the center of the connecting beam and is disposed parallel with and a predetermined distance from the substrate, and two receptor binding regions are formed on upper surfaces of two arms of the sensing plate.

4. The sensing switch of claim 3, wherein different receptors are respectively immobilized on the receptor binding regions.

5. A sensing circuit, comprising a plurality of the sensing switches of claim 1 arranged in series and/or in parallel, thus forming an 'AND' and/or an 'OR' logic circuit.

6. The sensing circuit of claim 5, performing sensing and analyzing at the same time in response to an output signal from the 'AND' and/or 'OR' logic circuits.

* * * * *

SEQUENCE LISTING

```
<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotides
<220> FEATURE:
<221> NAME/KEY: misc_feature
<222> LOCATION: (1)
<223> OTHER INFORMATION: nucleotide was modified with thiol group at C6
      position

<400> SEQUENCE: 1
agatcagtgc gtctgtacta gcaca                                           25
```